(12) United States Patent
Dovichi et al.

(10) Patent No.: US 9,465,014 B2
(45) Date of Patent: Oct. 11, 2016

(54) HIGH SENSITIVITY ELECTROSPRAY INTERFACE

(71) Applicant: University of Notre Dame du Lac, Notre Dame, IN (US)

(72) Inventors: Norman Dovichi, South Bend, IN (US); Liangliang Sun, South Bend, IN (US); Guijie Zhu, South Bend, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 0 days.

(21) Appl. No.: 14/679,009

(22) Filed: Apr. 5, 2015

(65) Prior Publication Data

US 2015/0233877 A1    Aug. 20, 2015

Related U.S. Application Data

(63) Continuation of application No. PCT/US2014/053522, filed on Aug. 29, 2014.

(60) Provisional application No. 61/871,562, filed on Aug. 29, 2013.

(51) Int. Cl.
*H01J 49/00* (2006.01)
*G01N 30/72* (2006.01)
*G01N 27/447* (2006.01)
*H01J 49/04* (2006.01)
*H01J 49/16* (2006.01)

(52) U.S. Cl.
CPC .... *G01N 30/7266* (2013.01); *G01N 27/44743* (2013.01); *H01J 49/0404* (2013.01); *H01J 49/0445* (2013.01); *H01J 49/167* (2013.01)

(58) Field of Classification Search
CPC  H01J 49/165; H01J 49/167; G01N 27/4473; G01N 27/44717; G01N 30/72; G01N 30/726
USPC ...................... 250/281, 282, 288, 423 R, 424
See application file for complete search history.

(56) References Cited

U.S. PATENT DOCUMENTS 4,885,076 A * 12/1989 Smith ............... H01J 49/165
204/451
5,115,131 A * 5/1992 Jorgenson ......... H01J 49/165
250/282

(Continued)

FOREIGN PATENT DOCUMENTS

WO    2013075081 A2    5/2013

OTHER PUBLICATIONS

Wojcik, et al ("Simplified capillary electrophoresis nanospray sheath-flow interface for high efficiency and sensitive peptide analysis," Rapid Comm. Mass Spectrom. 24, 2010, pp. 2554-2560).*

(Continued)

*Primary Examiner* — Michael Maskell
(74) *Attorney, Agent, or Firm* — Haukaas Fortius PLLC; Michael Haukaas

(57) ABSTRACT

The invention provides a sheath-flow interface for producing electrospray from a capillary. The electrospray generated by the interface can be used as the source of ions for mass spectrometry. Electrokinetic flow in the interface can move a sheath liquid past the end of a capillary so as to mix with an analyte effluent discharged from the capillary. The sheath liquid and analyte mixture can be directed to an electrospray emitter to generate an electrospray.

19 Claims, 15 Drawing Sheets

(56) References Cited

U.S. PATENT DOCUMENTS

| | | | |
|---|---|---|---|
| 5,245,186 | A | 9/1993 | Chait et al. |
| 5,423,964 | A * | 6/1995 | Smith .............. G01N 27/44717 204/452 |
| 5,504,329 | A | 4/1996 | Mann et al. |
| 2002/0175281 | A1* | 11/2002 | Valaskovic ........ G01N 30/7266 250/288 |
| 2005/0232929 | A1 | 10/2005 | Kadkhodayan et al. |
| 2007/0256935 | A1 | 11/2007 | Sugimoto et al. |
| 2008/0026949 | A1* | 1/2008 | Hoidal ................ C12Q 1/6883 506/6 |
| 2011/0042216 | A1 | 2/2011 | Maxwell et al. |
| 2013/0140180 | A1* | 6/2013 | Dovichi ........... G01N 27/44743 204/451 |
| 2015/0162177 | A1 | 6/2015 | McGivney |
| 2015/0233877 | A1* | 8/2015 | Dovichi ............. G01N 30/7266 250/282 |

OTHER PUBLICATIONS

International Search Report dated Dec. 18, 2014, Corresponding to Related PCT Application No. PCT/US2014/053522.
Li, Yihan et al., "Quantitative Multiple Reaction Monitoring of Peptide Abundance Introduced Via a Capillary Zone Electrophoresis-Electrospray Interface," Analytical Chemistry, 2012, 84, 6116-6121.
Li, Yihan et al., "Capillary Zone Electrophoresis-Electrospray Ionization-Tandem Mass Spectrometry as an Alternative Proteomics Platform to Ultraperformance Liquid Chromatography-Electrospray Ionization-Tandem Mass Spectrometry for Samples of Intermediate Complexity," Analytical Chemistry, 2012, 84, 1617-1622.
Moini, Mendi, "Simplifying CE-MS Operation. 2. Interfacing Low-Flow Separation Techniques to Mass Spectrometry Using a Porous Tip," Analytical Chemistry, 2007, 79, 4241-4246.
Mou, Si et al. "Accurate Determination of Peptide Phosphorylation Stoichiometry Via Automated Diagonal Capillary Electrophoresis Coupled With Mass Spectrometry: Proof of Principle," Analytical Chemistry, 2013, 85, 10692-10696.
Oesterle, Adair, "The Pipette Cookbook," Sutter Instrument Company.
Sun, Liangliang et al., "Capillary Zone Electrophoresis-Multiple Reaction Monitoring From 100 PG of Raw 264.7 Cell Lysate Digest," Analyst, 2013, 138, 3181-3188.
Sun, Liangliang et al., "CZE-ESI-MS/MS System for Analysis of Subnanogram Amounts of Tryptic Digests of a Cellular Homogenate," Proteomics, 2012, 12, 3013-3019.
Sun, Liangliang et al., "Fast Top-Down Intact Protein Characterization With Capillary Zone Electrophoresis-Electrospray Ionization Tandem Mass Spectrometry", Analytical Chemistry, 2013, 85m, 5989-5995.
Sun, Liangliang et al., "Integrated Capillary Zone Electrophoresis-Electrospray Ionization Tandem Mass Spectrometry System With an Immobilized Trypsin Microreactor for Online Digestion and Analysis of Picogram Amounts of Raw 264.7 Cell Lysate," Analytical Chemistry, 2013, 85, 4187-4194.
Wojcik, Roza et al., "Capillary Electrophoresis With Orbitrap-Velos Mass Spectrometry Detection," Talanta, 88 (2012), 324-329.
Wojcik, Roza et al., "Simplified Capillary Electrophoresis Nanosrpay Sheath-Flow Interface for High Efficiency and Sensitive Peptide Analysis," Rapid Communications in Mass Spectrometry, 2010, 24, 2554-2560.
Written Opinion dated Dec. 18, 2014, Corresponding to Related PCT Application No. PCT/US2014/053522.
Zhu, Guijie et al., "Capillary Isoelectric Focusing-Tandem Mass Spectrometry and Reversed-Phase Liquid Chromatography-Tandem Mass Spectrometry for Quantitative Proteomic Analysis of Differentiating PC12 Cells by Eight-Plex Isobaric Tags for Relative and Absolute Quantification," Analytical Chemistry, 2013, 85, 7221-7229.

* cited by examiner

HIGH SENSITIVITY ELECTROSPRAY INTERFACE

RELATED APPLICATIONS

This application is a continuation under 35 U.S.C. 111(a) of International Application No. PCT/US2014/053522 filed Aug. 29, 2014 and published in English as WO 2015/031820 on Mar. 5, 2015, which claims priority under 35 U.S.C. §119(e) to U.S. Provisional Application No. 61/871,562, filed Aug. 29, 2013, which applications and publication are incorporated herein by reference.

GOVERNMENT SUPPORT

This invention was made with government support under Grant No. R01GM096767 awarded by the National Institutes of Health. The government has certain rights in the invention.

BACKGROUND OF THE INVENTION

Bottom-up proteomics is a useful method to identify proteins and characterize their amino acid sequences and post-translational modifications by proteolytic digestion of proteins prior to analysis by mass spectrometry. Bottom-up proteomics is widely used for qualitative and quantitative characterization of complex biological samples. Given micrograms of material, it is possible to identify more than 10,000 proteins from mammalian cell lysates and over 2,500 proteins from prokaryote lysates. The performance of bottom-up proteomics degrades rapidly for mass-limited samples, such as laser capture microdissected tissues, circulating tumor cells, single embryos, and single somatic cells.

There have been a handful of reports of bottom-up proteomics of nanogram samples using capillary liquid chromatography (LC)-electrospray ionization (ESI)-tandem mass spectrometry (MS/MS). Mann's group identified 2,000 proteins from single pancreatic islets with protein content of several hundred ng (Waanders et al., Proc. Natl. Acad. Sci. U.S.A. 2009, 106, 18902). Karger's group identified 566 proteins from 50 ng of digest of *Methanosarcina acetivorans* (Yue et al., Anal. Chem. 2007, 79, 938) and 163 proteins from ~2.5 ng of the tryptic digest of a cervical cancer cell line (Luo et al., Anal. Chem. 2007, 79, 6174). Smith's group detected 870 proteins with an accurate mass and time tags (AMTs)[8] strategy from low nanogram amounts of the digest of *Deinococcus radiodurans* (Smith et al., Proteomics 2002, 2, 513). Smith's group also reported the detection of the three most abundant proteins in a 0.5 pg sample with the AMTs method, and reported a ~10 zmole detection limit for one peptide in a bovine serum albumin digest (Shen et al., Anal. Chem. 2004, 76, 144). Dovichi and co-workers used a Q-Exactive mass spectrometer with higher energy collisional dissociation (Olsen et al., Nat. Methods 2007, 4, 709) to identify ~100 protein groups from 1 ng of a digest of the RAW264.7 macrophage cell line (Sun et al., Rapid Commun. Mass Spectrom. 2013, 27, 157). All of these analyses required at least one hour of instrument time. Thus, faster methods for bottom-up analysis of femtogram amounts of protein digest would be a significant benefit to the proteomics community.

Capillary zone electrophoresis-electrospray ionization-tandem mass spectrometry (CZE-ESI-MS/MS) has attracted attention for bottom-up proteomics, and this approach consistently outperforms LC-MS/MS for low nanogram samples. The improved performance of CZE for small sample amounts presumably is due to its very simple design, eliminating sample loss on injectors and fittings. Beginning with the pioneering work of Smith's group (Smith et al., Anal. Chem. 1988, 60, 1948), electrospray interfaces have been developed for capillary electrophoresis (Maxwell et al., Anal. Chim. Acta 2008, 627, 25). However, new interfaces are needed to reduce sample dilution due to low sheath flow rates, to eliminate mechanical pumps, to tolerate a wide range of separation buffers, and to stabilize operation in the nanospray regime.

SUMMARY

The invention provides an ultrasensitive and fast capillary zone electrophoresis-electrospray ionization-tandem mass spectrometry (CZE-ESI-MS/MS) system based on an improved electrokinetically-pumped sheath-flow interface. The interface has several advantages, including reduced sample dilution due to a very low sheath flow rate, elimination of mechanical pumps, tolerance for a wide range of separation buffers, compatibility with commercial capillary electrophoresis instruments, and stable operation in the nanospray regime. The system is useful for rapid bottom-up analysis of femtogram amounts of protein digests and provides extremely high sensitivity.

Accordingly, the invention provides a sheath-flow interface for producing electrospray from a capillary, wherein the interface includes:

(a) a capillary configured to contain an analyte liquid, the capillary having an injection end configured to receive the analyte liquid and a distal end configured to expel analyte effluent wherein the outer diameter of a segment of the distal end tapers to a reduced outer diameter in the range of about 20 µm to about 200 µm;

(b) an electrospray emitter coaxially disposed surrounding at least the distal end of the capillary, the electrospray emitter having a distal end that is tapered to terminate at an opening, the opening being coaxially disposed in relation to the distal end of the capillary; and (c) a sheath liquid reservoir in liquid communication with an interior of the electrospray emitter, such that an electrically conductive sheath liquid can flow from the sheath liquid reservoir, through a connecting fixture intermediate the capillary and the electrospray emitter, across the distal end of the capillary, and through the opening at the distal end of the electrospray emitter.

The sheath-flow interface can be configured such that the distal end of the capillary and the electrospray emitter orifice are separated by a distance of about 750 µm to about 100 nm within the electrospray emitter. In embodiments where the outer diameter of the capillary is smaller than the emitter orifice diameter, the distal end of the capillary can be configured to reside within the emitter orifice opening. Furthermore, the distal end of the capillary can extend up to about 100 µm beyond the emitter orifice opening.

The sheath liquid can provide electrical contact between the capillary and the electrospray emitter. The sheath-flow interface can be configured to produce a nanospray generated by electrokinetic flow of the sheath liquid mixed with the analyte effluent. Furthermore, the electrokinetic flow can be generated by an electric potential between the electrospray emitter and a target surface disposed adjacent, but not in physical contact with, the opening of the emitter.

In various embodiments, the outer diameter of the distal end of the capillary can be about 20 µm to about 75 µm, or about 45 µm to about 65 µm. The segment of the distal end that tapers to a reduced outer diameter can be a segment length of about 0.1 mm to about 10 mm, typically about 5 mm.

The sheath-flow interface can detect a plurality of peptides from a 400 femtogram sample of peptides in less than 12 minutes, or less than 10 minutes, of mass spectrometry instrument time when configured with capillary zone electrophoresis and a tandem mass spectrometer. The peptides comprise peptide digests such as an *E. coli* tryptic digest.

The sheath-flow interface can be configured with a capillary zone electrophoresis instrument and a mass spectrometer, wherein greater than 150 peptides can be identified by accurate mass and time tags from sub-picogram amounts of a complex protein digest in less than 12 minutes of mass spectrometer time, often in less than 10 minutes of mass spectrometer time.

The mass spectrometer detection limit can be about 1-10 zeptomoles, for example, as low as approximately 1 zeptomole.

The invention also provides methods to analyze a protein digest comprising configuring the sheath-flow interface of claim 1 with a capillary zone electrophoresis instrument, wherein the analyte liquid is separated within a separation capillary by capillary zone electrophoresis, and about 10 kV of potential is applied to provide an electric field of about 300 V/cm, to produce a wide analyte separation window, during which time analytes migrate from the capillary into the interface within about 60 minutes. An average of 250,000 theoretical plates to about 350,000 theoretical plates are obtained for peptide separations.

In some embodiments, the inner diameter of the separation capillary of the sheath-flow interface is about 5 µm to about 75 µm. In various embodiments, the total flow rate for spray is about 15 to about 200 nL/minute, about 20 to about 200 nL/minute, about 15 to about 25 nL/minute, or about 20 nL/minute. The methods can include configuring the sheath-flow interface described herein with tandem mass spectrometry, wherein the sheath-flow interface is configured to provide the nanospray to a mass spectrometer for analysis, wherein the target surface is an input orifice of the mass spectrometer, and wherein the lower detection limit of protein samples is about 3 femtograms about 5 femtograms. The mass detection limit of peptides analyzed can be about 1 zeptomole, particularly when a small inner diameter separation capillary (e.g., less than about 15 microns, typically about 10 microns, in diameter). To achieve the very low mass detection limit, a highly sensitive mass spectrometer should be employed. One example of a highly sensitive mass spectrometer is the Q-Exactive Quadrupole-Orbitrap Mass Spectrometer (Thermo Fisher Scientific Inc.). The signal-to-noise ratio of peptides analyzed can be about 260:1 to about 300:1.

The invention further provides methods for producing a nanospray of an analyte effluent from a capillary using a sheath-flow interface described herein comprising applying a voltage to the sheath liquid reservoir sufficient to drive electroosmotic flow of the sheath liquid from the sheath liquid reservoir, through a connecting fixture intermediate the capillary and the electrospray emitter, across the distal end of the capillary, and through the opening at the distal end of the electrospray emitter, wherein the analyte effluent is separated within the capillary by capillary zone electrophoresis by applying a voltage to the injection end of the capillary.

In various embodiments, the analyte liquid can be moved through the capillary by an electrokinetic force or a mechanical pumping force. The analyte liquid can be separated within the capillary by capillary zone electrophoresis, micellar electrokinetic chromatography, capillary electrochromatography, capillary isoelectrofocusing, capillary liquid chromatography, or combinations thereof. The nanospray can be produced by, for example, electroosmotic flow. The analyte liquid can be separated within the capillary by electrophoresis, wherein the nanospray is produced by electroosmotic flow, and wherein both the electrophoresis and the electroosmotic flow are driven by applying an electric potential between the injection end of the capillary, the sheath liquid reservoir, and the target surface. The analyte liquid can be separated by chromatography where flow is driven by either a mechanical pump in conventional liquid chromatography or by electrokinetic flow in electrochromatograpy; in these cases, electrospray can be driven by electroosmotic flow within the emitter.

The sheath-flow interface can be configured to provide the nanospray to a mass spectrometer for analysis, and wherein the target surface is an input orifice of the mass spectrometer. The target surface can be held at ground, or the target surface can be held at a potential. The sheath liquid can be configured to enhance the compatibility of the analyte effluent with the mass spectrometer. The opening in the distal end of the electrospray emitter can be about 0.5 µm to about 50 µm in diameter, or about 0.5 µm to about 30 µm in diameter.

The invention also provides methods for analyzing biomolecules such as a protein digest. The methods can include forming an analyte effluent from a protein digest and producing a nanospray of the analyte effluent from a capillary using an embodiment of the sheath-flow interface described above. The methods of producing the nanospray of the analyte effluent can include applying a voltage to the sheath liquid reservoir sufficient to drive electroosmotic flow of the sheath liquid from the sheath liquid reservoir, through a connecting fixture intermediate the capillary and the electrospray emitter, across the distal end of the capillary, and through the opening at the distal end of the electrospray emitter. The analyte effluent can be separated within the capillary by capillary zone electrophoresis by applying a voltage to the injection end of the capillary.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

(FIG. 1A) Schematic illustration of a representative interface in accordance with disclosed embodiments. (FIG. 1B) Schematic of a representative interface with a mass spectrometer. The sheath liquid can be pumped by electrokinetic flow driven by the potential difference between HV2 and an inlet of the mass spectrometer. The separation can be driven by the potential difference between the inlet (HV1) and outlet (HV2) of the capillary.

FIG. 8B: peptide intensity from 16 pg amounts of E. coli_$1^{st}$ run vs. peptide intensity from 16 pg amounts of E. coli_$3^{rd}$; FIG. 8C: peptide intensity from 16 pg amounts of E. coli_$2^{nd}$ run vs. peptide intensity from 16 pg amounts of E. coli_$3^{rd}$ run). The peptide intensity was obtained from database searching results with MaxQuant software (v. 1.3.0.5), which is the summed eXtracted Ion Current (XIC) of all isotopic clusters associated with the identified peptide sequence.

(FIG. 14A) Entire separation; (FIG. 14B) detail of the separation from 12 to 18 minutes. Data were treated with a Lowess filter with Gaussian kernel and span of 10 points. The sample loading amount was ~60 ng; the capillary was 20 μm i.d. and 100 cm long; the separation buffer was 0.5% (v/v) FA; and a field strength of 280 V/cm was used for the separation.

DETAILED DESCRIPTION

Figure 1A:
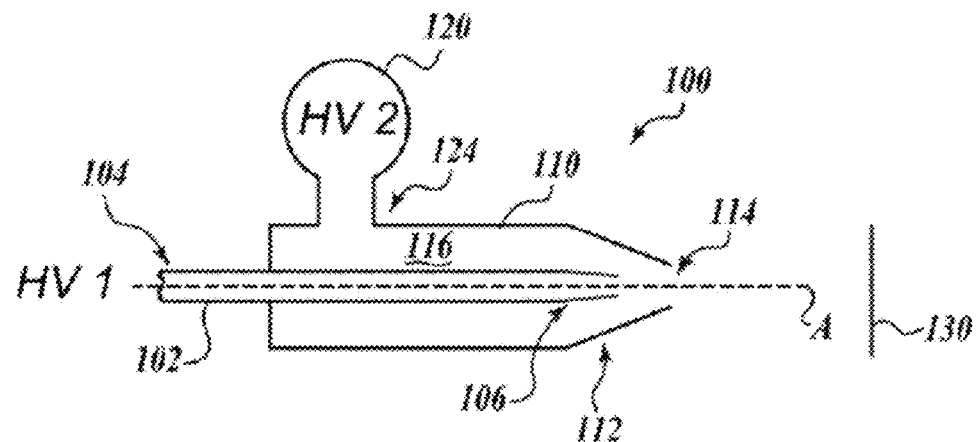
FIGS. 1A and 1B.

Described herein is an electrokinetically pumped sheath-flow electrospray interface and the demonstration of its use when coupled with capillary electrophoresis. For useful capillary electrophoresis systems, see Wojcik et al., *Rapid Commun. Mass Spectrom.* 2010; 24: 2554-60. A significant modification to previous interfaces is described herein, which modification provides roughly two orders of magnitude improved sensitivity. The improved interface has been used for the analysis of a variety of digests, including 400 femtograms of a tryptic digest of an E. coli lysate. In that digest, 154 peptides from over 60 proteins were identified in a 10 minute analysis. Mass detection limits for three peptides from the same protein are approximately 1 zeptomole (600 molecules). The improved interface produces a two-order of magnitude improvement in the state of art for bottom-up protein identification and a one-order of magnitude improvement in the state of art for MS-based peptide detection limits.

The importance of the tapered capillary arises in part from the dimensions of capillaries used in commercial electrophoresis instruments. Those instruments (e.g., Beckman instruments) typically use 375 micrometer outer diameter fused silica capillaries. Those capillaries are far too large to be used with the improved interface described herein because the standard capillary tips butt against the emitter when attempting to reduce the distance from the capillary tip to the emitter orifice. By modifying (e.g., reducing the outer diameter of) the distal end of capillaries, they become compatible with the interface described herein.

Definitions

The following definitions are included to provide a clear and consistent understanding of the specification and claims. As used herein, the recited terms have the following meanings All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more analytes can refer to one, one or two, one to three, one to four, one to five, 1-10, 1-100, or 1-500 different analytes or different types of analytes.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation. &p The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect, such as the minimum amount of a protein to obtain a mass spectrogram.

The term "nanospray" refers to a method of creating an aerosol of sub-micrometer-sized droplets, or the product of such process. Nanospray is a form of electrospray ionization in which an electrostatic field overcomes the surface tension of a liquid to form a liquid jet. Nanospray can employ glass capillaries with micrometer-sized exits and flow rates in the nL/minute range.

The term "electroosmotic flow" refers to the motion of liquid induced by an applied potential across a capillary tube, microchannel, or other fluid conduit.

Sheath-Flow Electrospray Interface

Hyphenation of capillary electrophoresis (CE) with electrospray ionization mass spectrometry (MS) was developed in the late 1980s and the combined use of the techniques has steadily developed since that time. Capillary electrophoresis-electrospray ionization interfaces generally fall into three categories: sheathless, co-axial sheath flow, and liquid junction interfaces.

The sheath flow interface uses a coaxial sheath liquid that mixes with analytes as they migrate from the separation capillary. The sheath liquid provides electrical contact between the electrophoretic separation and the electrospray ionization source. The sheath liquid can also modify the separation buffer to make it more compatible with MS detection. In the now commercially available sheath flow interface, the distal end of the separation capillary is inserted within a concentric tube, with the capillary's end extending beyond the tube. Electrical contact is made by a sheath liquid flowing over the capillary protruding from the tube, and a nebulizer gas is supplied to assist spray formation. The sheath liquid is pumped at a rate that maintains a stable spray and the interface operates at relatively high sheath flow rates, typically in the range of a few to several microliters per minute, which can result in significant sample dilution.

In a liquid junction interface, the separation capillary and electrospray emitter orifice are separated by a small gap. Electrical contact is made with this gap to drive the electrospray. Unfortunately, the gap can contribute to a loss of separation efficiency.

A sheathless interface eliminates sample dilution associated with the sheath liquid, which tends to result in higher sensitivity. In sheathless interfaces, the separation capillary often serves as the electrospray emitter. Ongoing research in the design of sheathless interfaces has focused on establishing electrical contact at the distal end of the separation capillary. Variations include coating the outer tip of the capillary with metal, inserting an electrode inside the capillary outlet, using porous etched capillary walls, and using a microdialysis junction. The major drawback of a sheathless interface is spray instability due to the very low flow rates produced from separation conditions, as well as the limited choices of separation buffers due to lack of post column chemistry.

To overcome some of the problems associated with both the original sheath flow and sheathless interface designs, a low flow version of a sheath flow interface was introduced. In this design, the separation capillary was inserted inside a tapered glass emitter. A second capillary was inserted inside the emitter, supplying sheath liquid, pumped at the rate of 1 µL/min. Electrospray voltage was supplied by a stainless steel wire inserted into the emitter.

Sheath flow interfaces with tapered emitters can operate in the nanospray regime, which is associated not only with supporting lower flow rates but also with better desolvation, enhanced sensitivity, and increased salt tolerance. However, attempting to produce a nanospray from CE effluent presents many technical issues that must be overcome in order to advance the field of capillary electrophoresis-mass spectrometry (CE-MS). Described herein are systems and methods to overcome these issues.

Accordingly, in one embodiment, the invention provides a sheath-flow interface for producing electrospray from a capillary. The interface can include (a) a capillary configured to contain an analyte liquid, the capillary having an injection end configured to receive the analyte liquid and a distal end configured to expel analyte effluent, wherein the outer diameter of a segment of the distal end tapers to a reduced outer diameter in the range of about 20 µm to about 200 µm, about 20 µm to about 100 µm, or about 40 µm to about 100 µm; (b) an electrospray emitter coaxially disposed surrounding at least the distal end of the capillary, the electrospray emitter having a distal end that is tapered to terminate at an opening, the opening being coaxially disposed in relation to the distal end of the capillary; and (c) a sheath liquid reservoir in liquid communication with an interior of the electrospray emitter, such that an electrically conductive sheath liquid is allowed to flow from the sheath liquid reservoir, through a connecting fixture intermediate the capillary and the electrospray emitter, across the distal end of the capillary, and through the opening at the distal end of the electrospray emitter.

The sheath liquid can provide electrical contact between the capillary and the electrospray emitter. The sheath-flow interface can be configured to produce a nanospray generated by electrokinetic flow of the sheath liquid mixed with the analyte effluent. The electrokinetic flow can be generated by an electric potential between the electrospray emitter and a target surface disposed adjacent, but not in physical contact with, the opening of the emitter. The interface can thus be used to produce electrospray from a capillary, which electrospray can be used as a source of ions for mass spectrometry analysis or other analytical techniques that can make use of an electrospray such as evaporative light scatter detection, inductively coupled plasma detection, and electrospray deposition of target molecules on a surface for subsequent analysis.

The sheath-flow interface can be further described with reference to FIG. 1A. The interface 100 includes a capillary 102. The capillary 102 includes an injection end 104 that is configured to receive an analyte liquid. The analyte liquid can be introduced into the capillary 102 at the injection end 104 by various means known to those of skill in the art. For example, the injection end 104 can be interfaced with a chromatography column, such that effluent from the chromatography column is injected into the capillary 102. Other methods for providing analyte to the capillary 102 include contacting the injection end 104 with a reservoir of analyte and performing electrokinetic, hydrostatic or hydrodynamic injection.

The capillary 102 has a distal end 106 that is configured to expel analyte effluent. The outer surface diameter of distal end 106 is reduced compared to the outer diameter of the rest of capillary 102. The distal segment of distal end 106 (e.g., the last 0.1-10 mm of the capillary 102) can have an outer diameter that is reduced by about 30% to about 90%, or by about 40% to about 75%, often by about 60%, while the inner diameter remains approximately the same. Thus, in embodiments where the outer diameter of capillary 102 is about 150 µm, the outer diameter of distal end 106 can be reduced to an outer diameter of about 20 µm to about 200 µm, about 20 µm to about 100 µm, about 40 µm to about 100 µm, about 60 µm, or about 50 µm.

Typically, the outer diameter of the distal end of the capillary is chemically reduced without affecting the inner diameter. In other embodiments, the inner diameter can also be reduced, for example, when the outer diameter is reduced by a heating and pulling technique. Other techniques for reducing the outer diameter of the distal end of the capillary include mechanical grinding and sand blasting.

Analyte effluent, as used herein, refers to the analyte that has passed through the length of the capillary 102 and is expelled from the distal end 106. The analyte effluent can be moved through the capillary 102 by various means such as by using an electrokinetic force (e.g., electroosmotic and/or electrophoretic flow).

Disposed around the capillary 102 is an electrospray emitter 110. The electrospray emitter is coaxially disposed around at least the distal end 106 of the capillary 102, such that the capillary 102 and an opening 114 of the electrospray emitter 110 are coaxially arranged along axis A, as illustrated in FIG. 1A. A distal end 112 of the electrospray emitter 110 is tapered from the tubular cylindrical body of the emitter 110 in order to form the opening 114.

Electrospray can be generated from the analyte effluent passing through the capillary 102 and through the opening 114 in the emitter 110. To produce the electrospray, a sheath liquid can be provided, flowing through the interior 116 of the emitter 110. The sheath liquid can be delivered to the interior 116 from a sheath liquid reservoir 120. A connecting fixture 124 can provide the liquid communication between the sheath liquid reservoir 120 and the interior 116.

To provide the electrospray, the sheath liquid can flow through the interior 116 of the emitter 110 past the distal end 106 of the capillary 102. When flowing past the distal end 106 of the capillary 102, the sheath liquid interacts with the analyte effluent expelled from the capillary 102 and forces the analyte effluent toward the opening 114. The electrospray generated thus includes a mixture of the analyte effluent and the sheath liquid.

The electrospray can be generated by applying at least a voltage HV2 between the sheath liquid reservoir 120 and the target surface 130. The voltage HV2 drives electroosmotic flow of the sheath liquid, using the zeta potential at the emitter 110 interior surface. The HV2 voltage can provide electrokinetic flow sufficient to generate an electrospray from the opening 114. The electrospray can be a nanospray. The target surface 130 can be held at ground or at a voltage.

In some embodiments, a voltage HV1 can be applied to the capillary 102. The electrospray can then maintained by the electric field at the emitter opening 114, which is generated by a combination of voltage HV1 and HV2, or a surface potential at the target surface 130. In such an arrangement, both HV1 and HV2 potentials contribute to the electric field at the emitter. Ideally, the potential at the emitter is only controlled by HV2. The resistance of the capillary is typically large enough that HV1 will have little effect on the electrospray. Instead, electrophoresis is driven by the difference in potential between HV1 and HV2. The HV2 voltage or the surface potential at the target surface 130 are additional sources of potential that can be regulated to maintain desired electric field at the emitter.

The capillary 102 can be used for capillary electrophoresis (CE). When the interface is configured for CE, the voltage dropped across HV1 to HV2 provides electrokinetic flow in the form of electrokinetic separation for the analyte or analytes passing through the capillary 102.

The sheath liquid can have electrical conductivity properties such that an electrical connection sufficient to drive the electrospray generating process is provided between the distal end 106 of the capillary 102 and the distal end 112 of the emitter 110. The current generated by electrospray can be proportional to the conductivity of the liquid. Representative sheath liquids include, for example, 10 mM formic acid or acetic acid in 50% methanol/acetonitrile or isopropanol. As would be recognized by those of skill in the art, the percentage of organic solvents can vary depending on the analytes of interest. Volatile salts, such as ammonium formate or ammonium acetate, can be added to sheath liquid.

The analyte can be a variety of composition of matter borne by the analyte liquid through the capillary 102. The analyte may be the analyte liquid itself, or the analyte may be dissolved within the analyte liquid. Alternatively, the analyte may be heterogeneously mixed with the analyte liquid. Representative analytes include polar small molecules and salts thereof, and large biomolecules (e.g., metabolites, peptides, proteins, lipids, glycans, and nucleic acids). Other analytes include pesticides, environmental contaminants, pharmaceuticals and their contaminants, metabolites, and the like.

Further details of the individual components of the interface 100 include the following.

The capillary 102 can be any suitable and effective capillary for providing an analyte effluent. Representative capillaries can be formed from glass (e.g., fused silica) or plastic and can be cylindrical bodies having a tubular form wherein the inner diameter of the capillary is on the order of about 0.5 microns to about 500 microns. In one embodiment, the inner diameter is about 5 microns to about 75 microns, 5 microns to about 25 microns, 5 microns to about 15 microns, or about 10 microns.

The emitter 110 can be formed from glass, fused silica, and any other suitable and effective material for emitters. Polymers, such as TEFLON, can also be used, as can ceramics and any non-conductive material that can be shaped to form the appropriate structure of an emitter 110 as described herein. The emitter 110 is typically a uniform cylinder prior to the taper towards the distal end 112. However, the emitter 110 can also be tapered throughout, or have a non-circular cross section.

The inner diameter of the emitter 110 must be larger than the outer diameter of the capillary 102 so as to allow the capillary to fit inside the emitter 110. The interior 116 of the emitter 110 is defined by the space between the outer surface of the capillary 102 and the inner surface of the emitter 110.

The opening 114 of the emitter 110 partially defines the shape and size of the electrospray generated. In one embodiment, the opening 114 in the distal end of the electrospray emitter is about 0.5 microns to about 30 microns in diameter. The opening 114 is typically circular, although in certain embodiments the opening is non-circular.

In one embodiment, the distal end of the capillary 106 and the distal end of the electrospray emitter 112 (i.e., opening 114, the electrospray emitter orifice) are separated by a distance of less than about 750 microns. In another embodiment, the distal end of the capillary 106 and the distal end of the electrospray emitter 112 are separated by a distance of less than about 700 microns, less than about 500 microns, less than about 250 microns, less than about 100 microns, less than about 50 microns, less than about 10 microns, less than about 5 microns, less than about 1 micron, or less than about 0.5 microns. The distance between the distal end of the capillary and the emitter can be as little as about 100 nm. In one embodiment, the distance between the distal end of the capillary and the emitter is about 150 microns to about 250 microns, or about 200 microns.

In another embodiment, the distal end of the capillary 106 can be configured to reside within the distal end of the electrospray emitter 112. In addition, the distal end of the capillary 106 can extend up to about 100 μm beyond the emitter orifice opening 114 provided that the outer diameter capillary 106 is smaller than the diameter of the emitter orifice opening 114. In some embodiments, the distal end of the capillary 106 can extend beyond the emitter orifice opening 114 by about 5 μm, by about 25 μm, by about 50 μm, by about 75 μm, or by about 100 μm, or by a range between any two of the preceding values. This configuration produces similar results as when the he distal end of the capillary 106 and the distal end of the electrospray emitter 112 are separated by a distance of less than about 750 microns.

Figure 2:
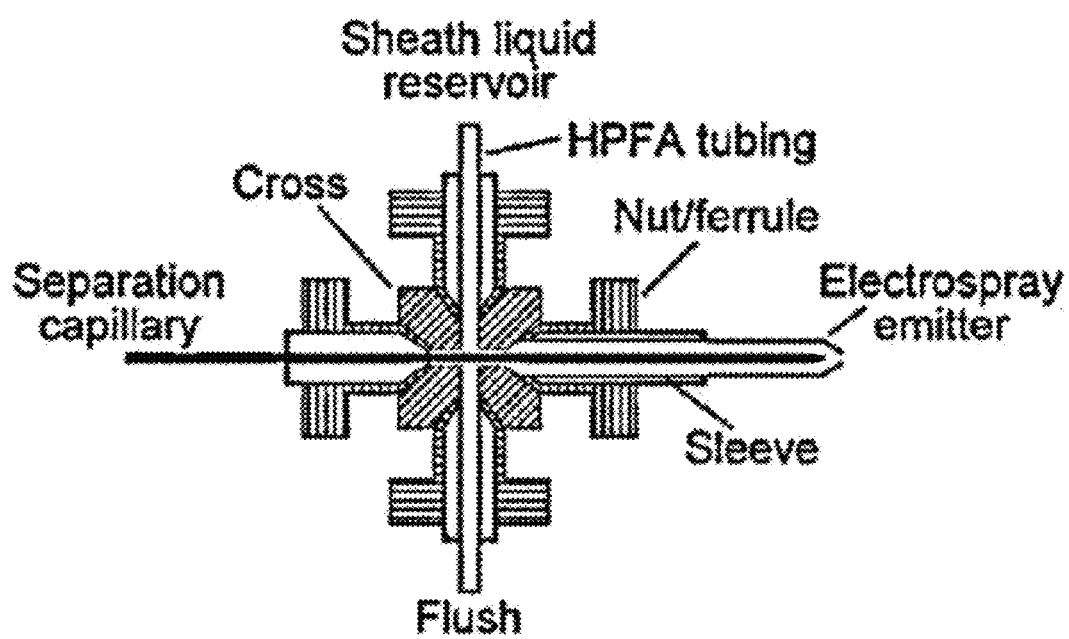
FIG. 2. Components of an interface, according to one embodiment.

Valves, tubing, and other fluidic control components can be used as the connecting fixture 124. An example of a representative connecting fixture 124 is illustrated in FIG. 2. The connecting fixture 124 can be made of TEFLON or other polymer tubing, glass, or fused silica. A switching valve can be incorporated to switch between multiple sheath fluids (i.e., between multiple sheath liquid reservoirs 120), if desired. The dimensions of the connecting fixture 124 are tied to the dimensions of the capillary 102 and the emitter 110. Representative inner diameters are about 10 μm to about 5 mm, and a length of about 1 mm to about 30 cm.

Electrical potential typically drives the operation of the interface 100. One embodiment provides the application of a potential, HV2, at the sheath liquid reservoir 120, with a ground or counter potential at the target surface 130. HV2 can be applied to the sheath liquid reservoir 120 in a number of ways, such as by electrical contact to an electrode disposed in the sheath liquid reservoir 120. For example, a wire electrode can be submerged in the sheath liquid reservoir 120 or an electrode can be disposed on a wall of the sheath liquid reservoir 120.

In one embodiment, the analyte liquid is moved through the capillary by a force such as an electrokinetic force or a mechanical pumping force. Electrokinetic forces are well known to those of skill in the art and include, but are not limited to, dielectrophoresis, and electroosmotic or electrophoretic flow.

When electrokinetic flow is used, the optional voltage HV1 can be used. HV1 can be applied by making electrical contact to the analyte liquid. For example, an electrode may be disposed at the injection end 104 of the capillary 102, or a wire electrode can be used to contact the analyte liquid near the injection end 104.

The analyte liquid can be separated within the capillary by techniques such as capillary zone electrophoresis, capillary electrochromatography, dielectrophoresis, or combinations thereof. The analyte liquid can be separated by liquid chromatography prior to entering the injection end of the capillary. The analyte liquid need not always be separated when traveling through the capillary. Instead, the capillary may receive pre-separated effluent and simply transport the analyte in order to generate the electrospray. Various chromatographic techniques can be used to provide the analyte liquid to the capillary, as long as the effluent of the chromatographic process can be provided and interfaced with the injection end of the capillary.

In one embodiment, the analyte liquid is separated within the capillary by electrophoresis, wherein the nanospray is produced by electroosmotic flow, and wherein both the electrophoresis and the electroosmotic flow are driven by applying an electric potential between the injection end of the capillary, the sheath liquid reservoir, and the target surface.

Figure 1B:
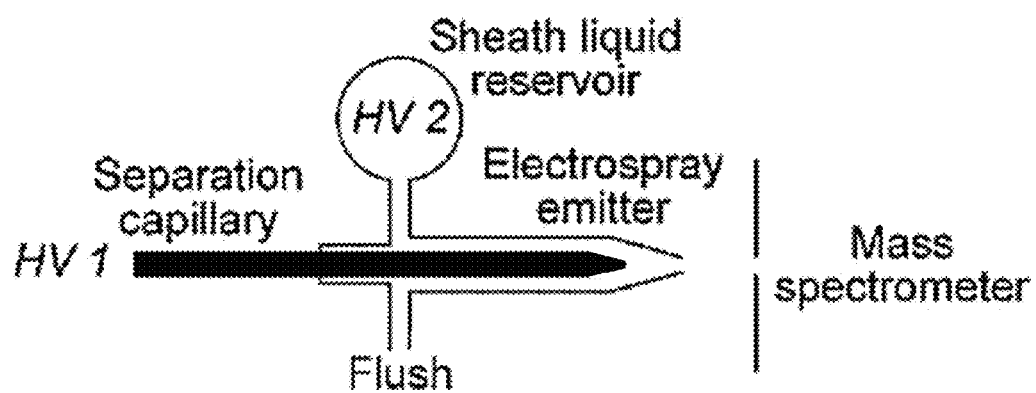

In some embodiments, the sheath-flow interface 100 is configured to provide the nanospray to a mass spectrometer for analysis (see FIG. 1B). In this embodiment, the target surface 130 is an input orifice of the mass spectrometer. Such a configuration is described in greater detail in the examples below.

When the interface 100 is used for mass spectrometry, the sheath liquid can be configured to enhance the compatibility of the analyte effluent with the mass spectrometer. If analyte effluent is not by itself compatible with MS, the sheath liquid can be selected so as to facilitate effective MS. For example, if CE is used to provide the analyte effluent, some common buffers may not be compatible with MS. However, if a proper sheath liquid is used, the buffer and analyte contained therein can be analyzed by MS.

The invention also provides methods for producing a nanospray of an analyte effluent from a capillary using a sheath-flow interface as described herein. In one embodiment the method comprises applying a voltage to the sheath liquid reservoir sufficient to drive electroosmotic flow of the sheath liquid from the sheath liquid reservoir, through a connecting fixture intermediate the capillary and the electrospray emitter, across the distal end of the capillary, and through the opening at the distal end of the electrospray emitter. The analyte effluent can be separated within the capillary by capillary electrophoresis by applying a voltage to the injection end of the capillary. However, in other embodiments, the analyte effluent is separated by liquid chromatography (or other separation method) prior to entering the capillary. In yet other embodiments, the analyte effluent is not separated either before entering or while traveling through the capillary. As described above, the interface can be used as an ionization source for mass spectrometry where the electrospray is ionized and directed into an input orifice of a mass spectrometer for analysis.

Design and Testing of CE-MS Nanospray Interface

This disclosure provides a nanospray sheath flow interface in which a stable spray is achieved with very low sheath flow rates, optionally without a pump or nebulizer gas. The separation capillary can be placed inside an emitter, such as a tapered glass ES emitter. Sheath liquid can be driven by electroosmosis produced by the zeta potential at the emitter surface. The sheath liquid flows over the end of the separation capillary, closing the circuit and mixing with the capillary effluent inside the tip. The capillary, the electrospray emitter, and sheath liquid tubing can be connected, for example, by a PEEK cross. A small emitter tip size (2 to 10 µm i.d.) allows for operation in the nanospray regime.

In previous interface designs, electrospray voltage is applied directly to the electrospray tip, which often requires the use of metal or metal-coated emitters or a wire electrode inside an emitter. The lifetime of these metal-coated emitter is finite and they often must be replaced. Although metal emitters are more robust than glass, redox reactions on the metal surface often lead to bubble formation and corona discharge, which limits the electrospray sensitivity and stability. Wire electrodes also have their limitations. For example, they can create turbulent flow and loss of separation efficiency. Carbon-coated and conductive polymer coated capillaries have been used to supply current to the tip. However, carbon coatings have limited lifespans and must be periodically replaced. Furthermore, conductive polymers must be applied to the exterior of the emitter, which applications may lead to emitter tip blockage. These problems can be circumvented by applying voltage to the tip indirectly, for example, by a platinum electrode placed in a sheath buffer reservoir.

Interface. A schematic of an interface is shown in FIG. 1B. The separation capillary can be threaded into a glass electrospray emitter using a cross fitting (e.g., 5-mm-long cross channels with 0.5 mm i.d.). One arm of the cross can be fitted with HPFA tubing (0.5 mm i.d.) that has been dipped into a microcentrifuge tube, which acts as the sheath liquid reservoir. The height of the liquid in the reservoir can be kept at the same height as the emitter tip to avoid hydrodynamic flow. High voltage can be applied to the injection end of the capillary (HV1) and to the sheath liquid reservoir (HV2). The separation can be driven by the difference in these potentials. HV2 can provide the potential that drives electro-osmotic flow in the emitter. The mass spectrometer inlet can be held at ground potential. The other arm of the cross can be used to flush the interface with sheath fluid at the start of an experiment.

In various embodiments, electrospray emitters can be pulled from 10 cm long borosilicate glass capillaries (1 mm o.d., 0.75 mm i.d.), for example, with a P-1000 Sutter Puller. The tip sizes used can range from about 2 µm to about 50 µm i.d., or about 2 µm to about 10 µm i.d., with a taper length of about 3 mm. The tip diameter can be determined by inspection of the tip under a microscope. The outer diameter of the tip can be noted, and the inner diameter can be determined based on the ratio of the inner to outer diameter of the initial glass capillary.

A detailed drawing of one example of an interface is shown in FIG. 2. A fused silica separation capillary (50 µm i.d., 150 µm o.d., 45 cm long) can be threaded through a PEEK coned port cross (Upchurch). The capillary is then threaded into the electrospray emitter. The capillary and emitter tip can be held in place with a sleeve, ferrule, and matching nut. The distance from the capillary tip to the emitter tip can be adjusted while viewing the system under a microscope as the fittings are tightened. Sheath liquid is introduced into the electrospray tip by an HPFA tubing connected to the cross. The fourth port of the cross can be connected to a syringe and used to flush the interface with sheath liquid at the start of an experiment.

Voltage can be delivered from a power supplies (e.g., a Spellman CZE 1000R) by platinum electrodes that are in contact with the running buffer and to the sheath liquid reservoir. The cross can be attached to a translation stage placed at the source of a Thermo LCQ ion trap instrument.

CE-MS. CE-MS experiments can be performed with instruments such as a Thermo Finnigan LCQ ion trap instrument. Samples can be biomolecules, such as an enzyme or peptide. Capillaries can be conditioned with 0.1 M HCl, followed by 1 M NaOH, and then separation buffer, all injected under 10 psi pressure for 5 minutes before use.

In continuous infusion experiments, the sample can be electrokinetically introduced into the separation capillary. Continuous infusion can be used to tune the instrument for optimal peptide signal. For capillary electrophoresis analysis, samples can be electrokinetically injected. In various experiments, the emitter tip can be placed about 2 mm away from the ion source. One set of effective tuning parameters include a lens voltage of −38 V and capillary temperature of 165° C.

In positive ion mode experiments, the separation buffer can be, for example, about 10 mM ammonium acetate, pH 7.8, and the sheath liquid can be an equal volume mixture of about 10 mM aqueous acetic acid and methanol.

In negative ion mode experiments, an Ultratrol LN (Target Discovery, TM) coating can be applied to the capillary to minimize electroosmotic flow. The separation buffer can consist of 10 mM ammonium acetate, pH 8, and the sheath liquid can be an equal volume mixture of 10 mM aqueous ammonium acetate and methanol.

With equal electroosmotic flow, the ratio of the electric potential of separation buffer and sheath liquid can be proportional to the ratio of the separation buffer and sheath liquid flow rates.

Distance Between Capillary Exit and the Emitter Tip. The distance from the capillary exit to the emitter exit significantly affects the performance of the ESI emitter. U.S. Patent Publication No. 2013/0140180 (Dovichi et al.) describes a sheath-flow interface and experiments were performed where the distance between the distal end of the separation capillary and the tip of the emitter was reduced from 2 mm to 1 mm, which narrowed and increased peak amplitude as a result of reduced extra-column band broadening. However, when using the apparatus and techniques of U.S. Patent Publication No. 2013/0140180 (Dovichi et al.), the inner diameter of the tip of the emitter and the outer diameter of the capillary resulted in a physical barrier that prevented the distal end of the capillary from approaching closer than 800 µm from the tip of the emitter. This extremely close proximity of the outer diameter edge of the distal end of the capillary and the inner diameter of the tip of the emitter resulted in degraded system performance, including decreased signal amplitude, broader peaks in chromatographic performance, and decreased plate count.

Attempting to bring the distal end of the capillary closer to the emitter tip is physically prevented by contact with the emitter wall. This problem is particularly serious when using large (e.g., 375 micron) outer diameter capillaries found in many commercial electrophoresis instruments. Those capillaries require separation distance between the capillary exit and the emitter orifice of several millimeters, which dramatically decreases sensitivity. Bringing the distal end of these large outer diameter capillaries closer to the emitter tip can result in breakage of the capillary tip, requiring disassembly and reassembly of the instrument.

Figure 3A:
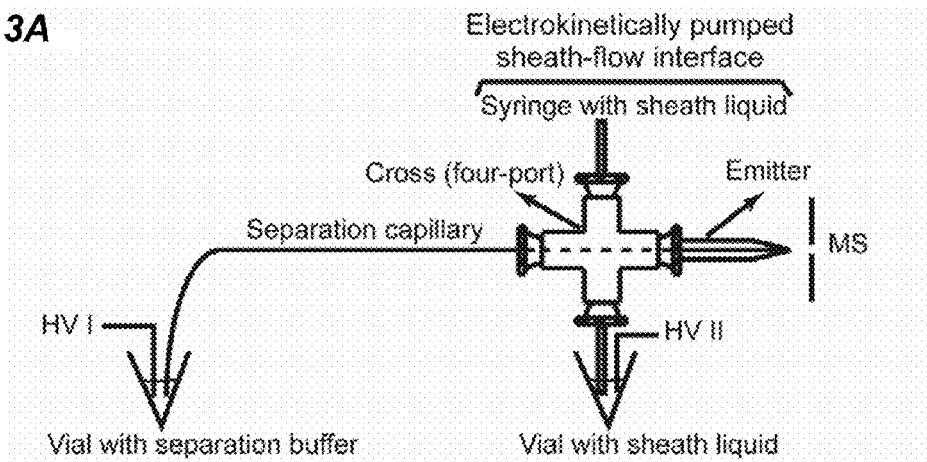
FIGS. 3A-C. CZE-ESI-MS/MS system. Sketch of the system (FIG. 3A), sketch of the etched capillary in the electrospray emitter (FIG. 3B), and micrograph of the etched capillary in the emitter (FIG. 3C).
Figure 3B:
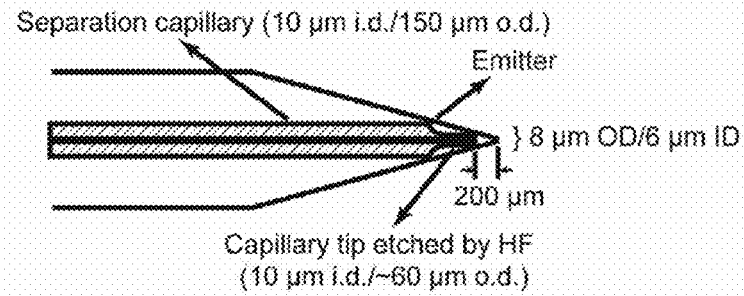

Solutions to this problem are described herein, whereby reducing the outer diameter of the capillary, such as by etching the outer diameter of a glass capillary, the distal end of the capillary can be brought closer to the emitter orifice. By careful etching of the outer surface of the capillary, the capillary can be brought as close as 100 nm from the tip of the emitter (i.e., by further etching of the embodiment illustrated in FIG. 3B). When the distal end of the capillary is modified such that its outside diameter is smaller than the diameter of the emitter orifice, the tip of the emitter can also be configured to reside within the emitter orifice and up to 100 microns beyond the emitter orifice. This shorter spacing between the tip of the separation capillary and the tip of the emitter, or its extension through the emitter orifice, results in significantly less extra-column band broadening.

Unexpectedly, the modification resulted in a two-order of magnitude improvement in the state of art for bottom-up protein identification and a one-order of magnitude improvement in the state of art for MS-based peptide detection limits. The increased sensitivity allows detection of peptides from very small amounts of sample. In addition, given the same amount of material, this interface will allow detection of more peptides and proteins than the conventional design. Also unexpected was the cleaner background from the mass spectrometer detection and the longer spray emitter lifetime. The modifications to the interface result in an interface such that very small sample sizes (e.g., 4-400 fg of peptides) can be analyzed in less than 12 minutes of mass spectrometer instrument time. Mass spectrometer detection limits as low as about 1 zeptomole (~600 molecules) can be obtained, thus masses as low as approximately 1 attogram can be detected. Accordingly, the enhanced sensitivity allows for the analysis of smaller samples, as described herein, and to identify more peptides from the same size sample used with previous interface designs.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1.

Ultrasensitive and Fast Bottom-Up Analysis of Femtogram Amounts of Complex Proteome Digests Capillary zone electrophoresis was coupled with an improved sheath-flow electrospray interface to produce a two order of magnitude improvement in the amount of material required for bottom-up protein analysis. This example describes an ultrasensitive capillary zone electrophoresis-mass spectrometry system based on the improved nanospray interface. The system can be used for analysis of picogram to femtogram amounts of digests such as *E. coli* digests. Over 100 proteins were identified based on tandem mass spectra from 16 pg digests; over 60 proteins were identified from 400 fg digests based on accurate mass and time tags in 10 minutes.

Bottom-up proteomics of nanogram samples using capillary liquid chromatography (LC)-electrospray ionization (ESI)-tandem mass spectrometry (MS/MS) analyses requires at least one hour of instrument time. In this example we report an ultrasensitive and fast capillary zone electrophoresis (CZE)-ESI-MS/MS system based on an improved electrokinetically-pumped sheath-flow interface. We demonstrate the system for the rapid bottom-up analysis of femtogram amounts of the E. coli protein digest.

CZE-ESI-MS/MS consistently outperforms LC-MS/MS for low nanogram samples, in part because of its improved interface. This example describes the development of another interface based on an electrokinetically pumped sheath-flow interface (FIG. 3A) (see Wojcik et al., *Rapid Commun. Mass Spectrom.* 2010, 24, 2554 for an example of a previous sheath-flow interface). The new interface has several advantages, including reduced sample dilution due to a very low sheath flow rate, elimination of mechanical pumps, tolerance for use of a wide range of separation buffers, and stable operation in the nanospray regime. We have also coupled CZE to a triple-quadrupole mass spectrometer with an interface for quantification of Leu-enkephalin in a complex mixture using multiple-reaction monitoring, and we obtained a 335 zmole peptide detection limit, indicating this system's ability for high sensitivity analysis (Li et al., *Anal. Chem.* 2012, 84, 6116).

A COMSOL model of the electrokinetically pumped sheath-flow interface predicted and experiments verified that sensitivity increases as the distal end of the capillary is brought closer to the emitter orifice. A typical minimum distance between the capillary tip and orifice is about 1 mm when using 150 micrometer outer diameter capillary and 2.5 mm when using 375 micrometer outer diameter capillary. The lower threshold of the distance is limited by the outer diameter of the separation capillary, which eventually butts against the interior of the conical emitter wall.

Figure 3C:
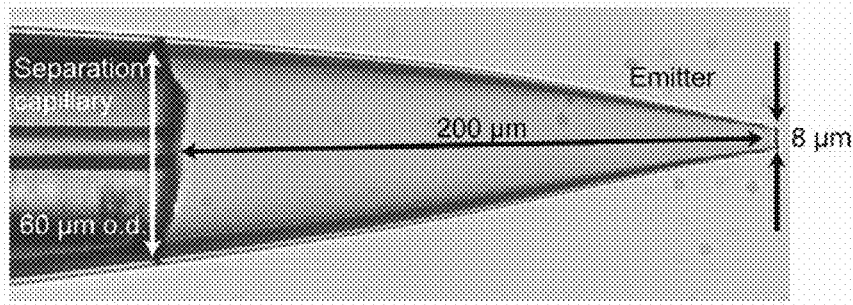

As described herein, we etched a few millimeters of the outside of a separation capillary tip with hydrofluoric acid to reduce its outer diameter from about 150 μm to about 60 μm or about 50 μm. This simple step allows us to place the capillary end much closer to the emitter orifice (e.g., ~200 μm) (FIG. 3B and 3C), which results in a dramatic improvement in the system's sensitivity. We used uncoated fused silica capillaries (32 cm and 40 cm, 10 μm i.d./150 μm o.d.) for electrophoresis, and a Q-Exactive mass spectrometer for peptide identification. Experimental details are provided in the Experimental section of this example below.

Preparation of silica capillaries are described in the Sutter Instrument Company Pipette Cookbook (2011, Novato, Calif., http://www.sutter.com/contact/faqs/pipette_cookbook.pdf). These capillaries can then be etched to provide capillaries for the interface described herein. An example of a useful capillary according to one embodiment is a capillary with the following dimensions: 25-30 cm long, 10 μm i.d./150 μm o.d., with an etched end (~5 mm long, ~50-60 μm o.d.). For capillaries with larger outer diameters (e.g., 250-300 μm o.d.), the outer diameter of the etched end can be reduced to about 200 μm o.d., for example, where the capillary emitter is configured to allow the distal end of the capillary to reside less than about 750 μm from the emitter orifice. The distal ends of capillaries can also be etched such that the outer diameter is reduce to about 20 μm to about 100 μm, about 20 μm to about 80 μm, about 40 μm to about 80 μm, about 60 μm to about 80 μm, about 40 μm to about 60 μm, or about 50 μm to about 60 μm.

We first evaluated the effect of separation voltage for the analysis of 28 pg amounts of E. coli digests. Separations were performed at 15 kV (500 V/cm) and 10 kV (300 V/cm) in a 32 cm-long capillary. Electropherograms were generated with MaxQuant software (v. 1.3.0.5) (*Nat. Biotechnol.* 26, 1367-1372 (2008)). The 10 kV potential produced a wider separation window, which resulted in significantly more protein (129±18 vs. 88±14) and peptide (375±27 vs. 246±19) identifications compared with 15 kV. The following work used an electric field of 300 V/cm.

We then evaluated the reproducibility of our CZE-ESI-MS/MS system for analysis of 16 pg of the E. coli protein digests with a 40 cm capillary. We identified 105±17 proteins and 256±9 peptides based on triplicate bottom-up analysis of tandem mass spectra. The state of the art for tandem mass spectra analysis of complex protein digests is ~100 protein identifications at the 1 ng level. Our system produced a similar number of protein identifications from two-orders of magnitude less sample.

Figure 4:
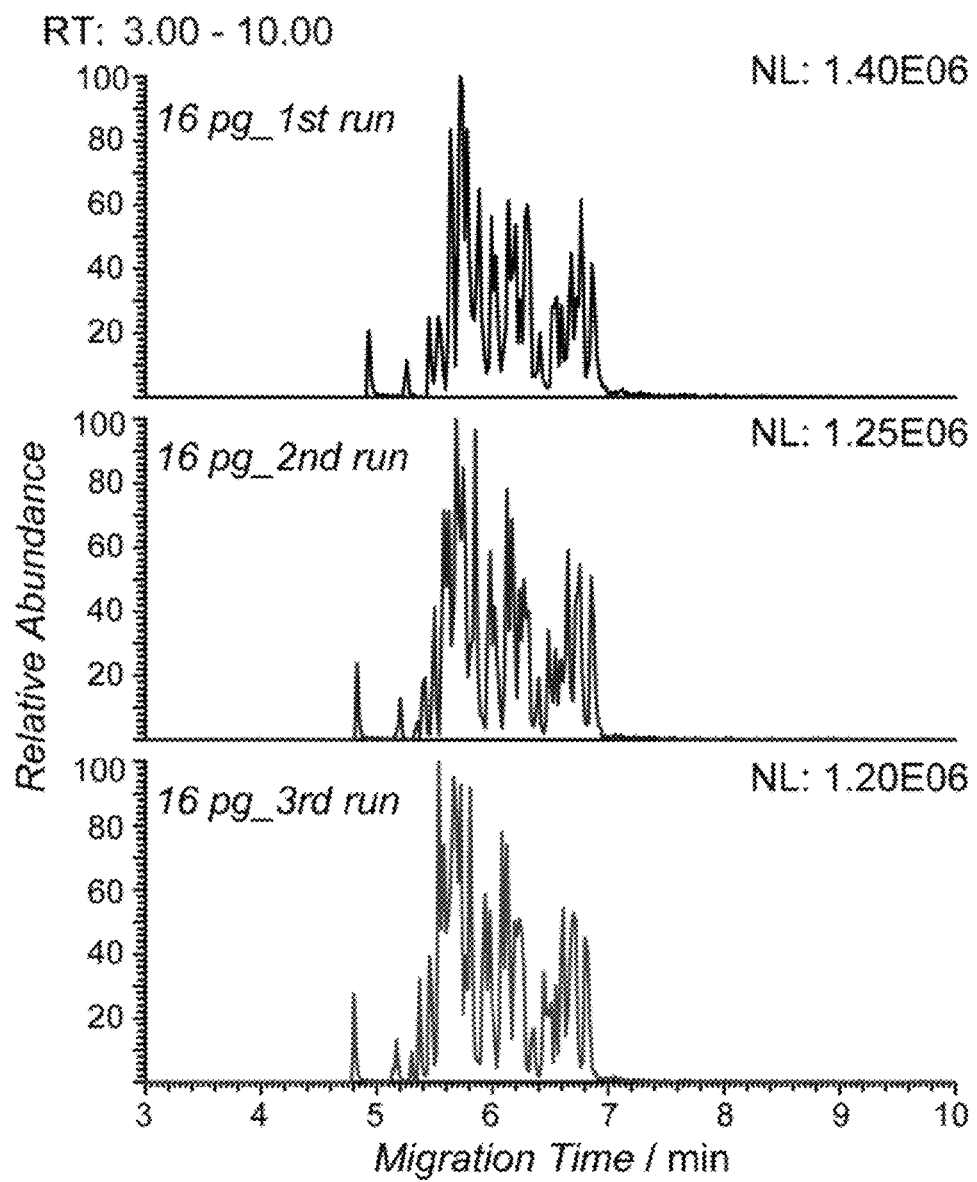
FIG. 4. Extracted ion electropherograms of 50 high intensity peptides identified based on tandem spectra from 16 pg amounts of E. coli digests analyzed by CZE-ESI-MS/MS in triplicate. The mass tolerance for extraction was 2 ppm.
Figure 5:
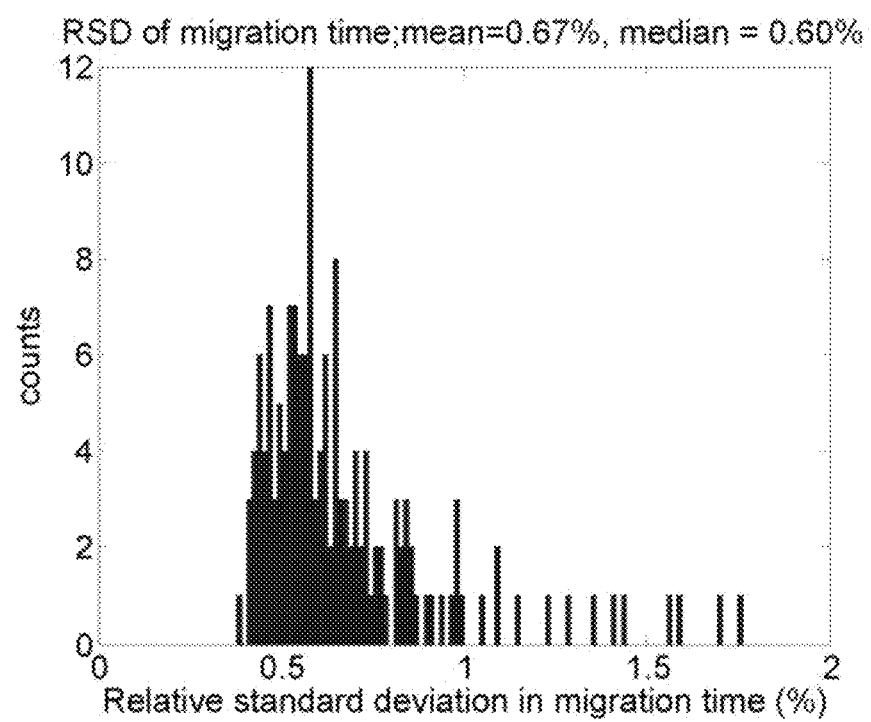
FIG. 5. Relative standard deviation (RSD) distribution of peptide migration time for triplicate runs of 16 pg of E. coli digests. Selected ion electropherograms were generate from 154 high intensity peptides. The mass tolerance used for peptide peak extraction was 3 ppm. A Gaussian function was fit to the electropherograms using an unsupervised nonlinear least squares fit: Intensity(t)=a×exp−0.5*(t−$t_0$)$^2$/width$^2$+offset; where t is time, $t_0$ is the peak migration time, a is peak amplitude, width is the peak's width in terms of the standard deviation of the Gaussian, and offset is a dc offset. MATLAB's fit routine was used for the calculation. The amplitude and migration time for the maximum point in each electropherogram was used for the initial guesses of a and $t_0$. The initial guess for width was 3 seconds. The initial estimate for offset was the median value of the electropherogram. The relative standard deviation in migration time was calculated as std($t_0$)/mean($t_0$)×100% for each set of triplicate electropherograms.
Figure 6:
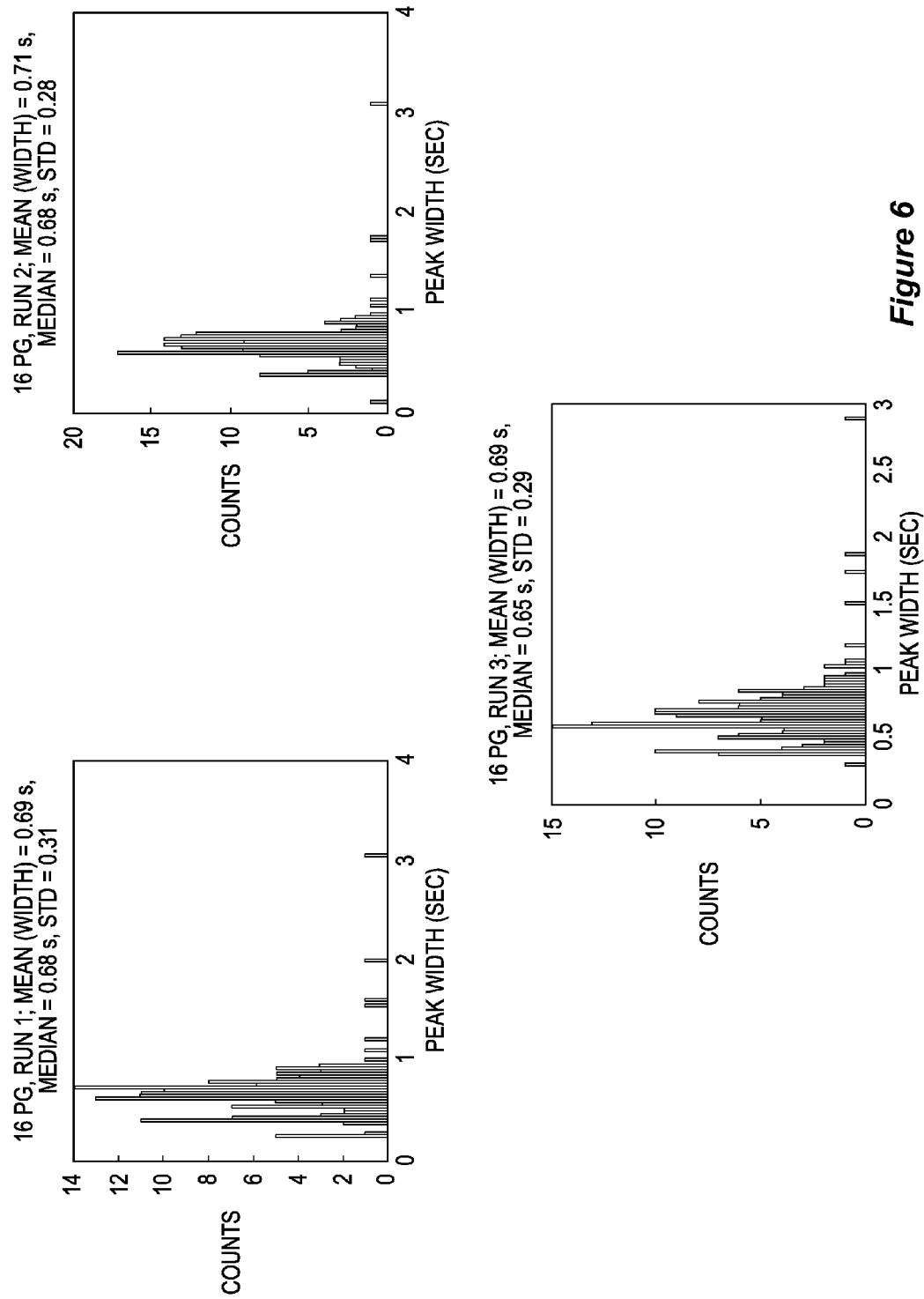
FIG. 6. Peak width distribution of identified peptides from 16 pg amounts of E. coli digests with CZE-ESI-MS/MS in triplicate. Peak width was determined from the nonlinear regression analysis described in the description for FIG. 5 above. The full width at half height for a Gaussian function=2.35×width, and the full width at baseline is 4×width.
Figure 7:
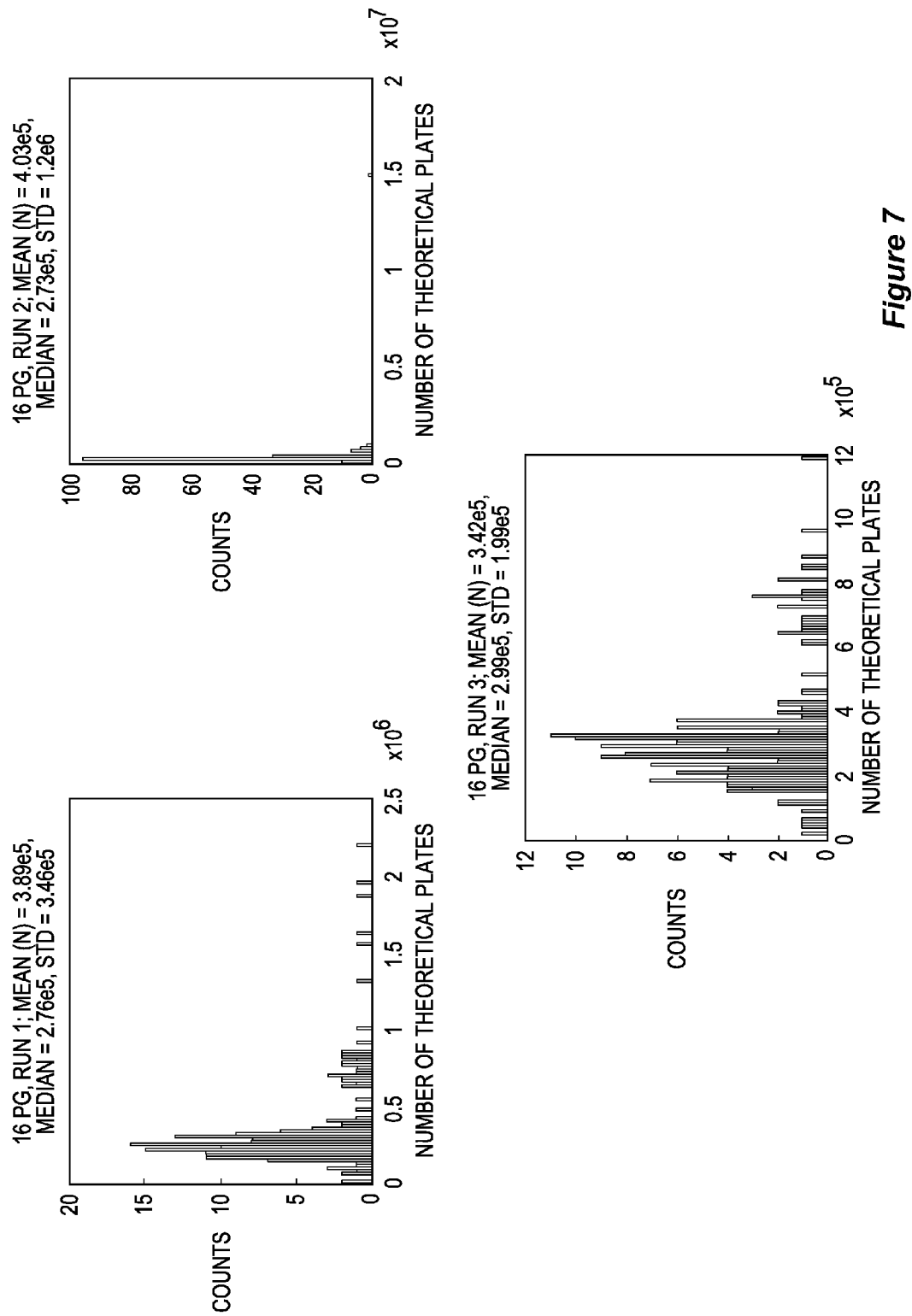
FIG. 7. Distribution of the number of theoretical plates (N) for peptides identified from 16 pg amounts of E. coli digests with CZE-ESI-MS/MS in triplicate. The number of theoretical plates was calculated as N=($t_0$/width)$^2$ where $t_0$ and width were determined in the nonlinear regression analysis described in the description for FIG. 5 above.
Figure 8A:
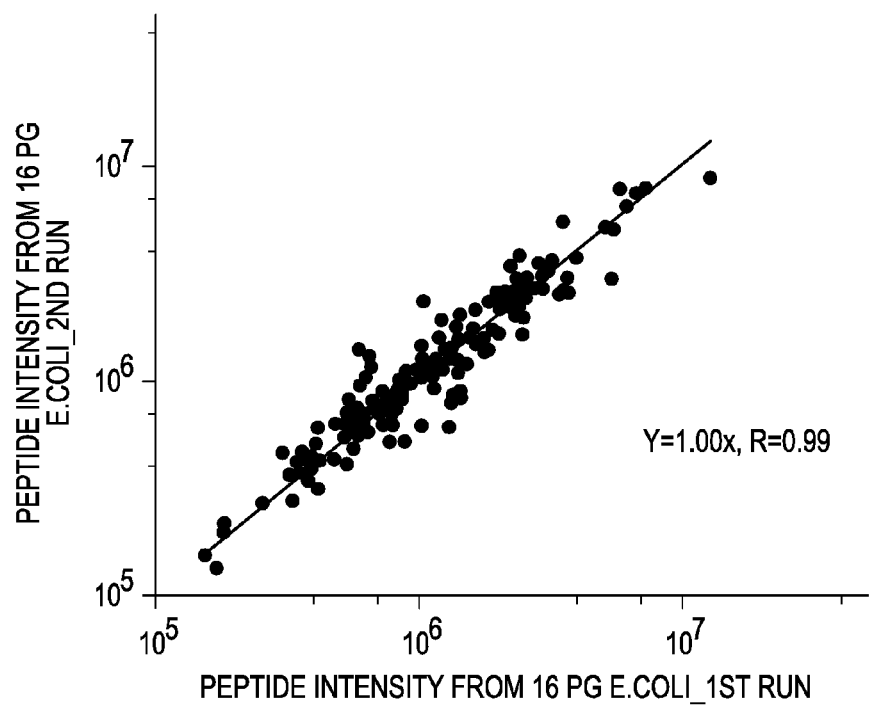
FIG. 8A-C. Correlation of peptide intensities between runs from 16 pg amounts of E. coli digests analyzed (FIG. 8A: peptide intensity from 16 pg amounts of E. coli_$1^{st}$ run vs. peptide intensity from 16 pg amounts of E. coli_$2^{nd}$ run.
Figure 8B:
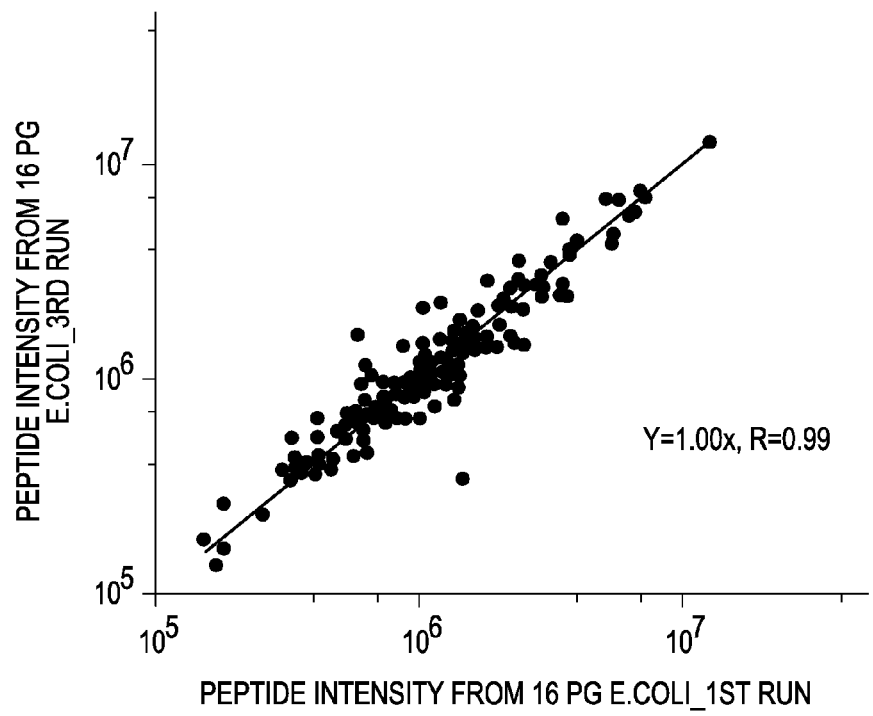
Figure 8C:
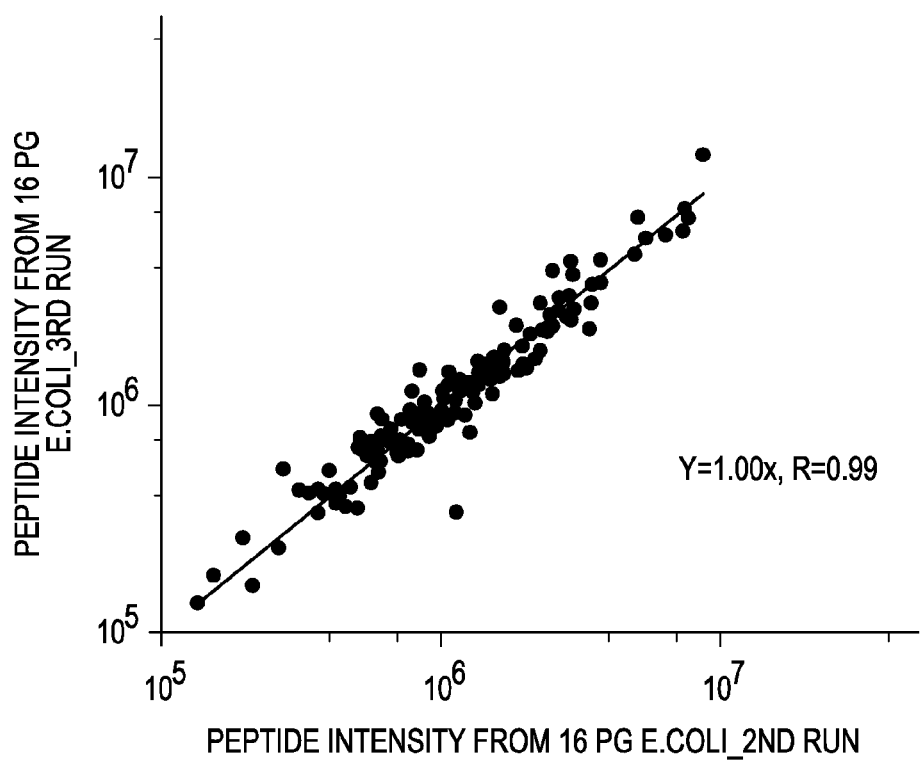

The separations were reproducible and efficient. The signals from 50 peptides were summed to produce extracted ion electropherograms (FIG. 4). The average relative standard deviation of the migration time of 154 peptides was 0.7% (FIG. 5) The electrophoretic peaks were quite sharp, with an average width, defined as the standard deviation of the Gaussian function used to fit the peaks, of 0.7 s (1.6 s full width at half height) (FIG. 6). We consistently obtained an average of over 300,000 theoretical plates for the peptide separations (FIG. 7). Peak intensity was also consistent between runs (FIG. 8). Separations were complete in less than 10 minutes, which is an order of magnitude improvement in analysis time compared to the state-of-the-art for high sensitivity bottom-up proteomics of complex proteomes.

Figure 9A:
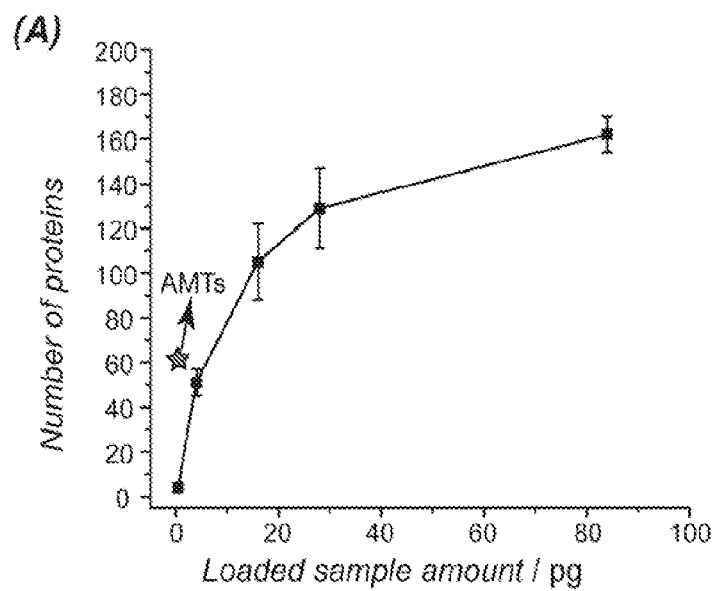
FIG. 9A-B. Relationship between loaded amounts of E. coli digests and identifications based on tandem spectra (points connected by lines) and accurate mass and time tags (star=AMTs). Protein identifications (FIG. 9A); peptide identifications (FIG. 9B). Each sample was analyzed in duplicate or triplicate. The identifications based on AMTs from 400 fg amounts of E. coli digests were labelled with star. The error bars are standard deviations of the mean.
Figure 9B:
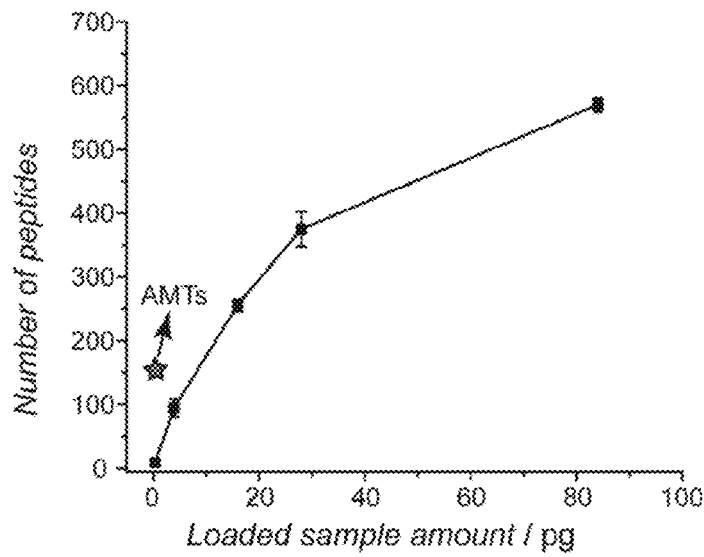

We next determined the relationship between the number of identifications based on tandem mass spectra and the loaded amounts of E. coli digests (FIG. 9). In duplicate 400 fg loadings, nine peptides corresponding to 4±1 proteins were confidently identified after manual evaluation of tandem mass spectra. The most abundant protein in E. coli, elongation factor Tu, makes up ~1% of the total protein mass. An analysis of 400 fg of an E. coli digest will thus contain about 4 fg of this protein. The minimum protein amount for identification by tandem mass spectrometry is less than 4 fg, thus representing an improvement of two orders of magnitude in the state of art (Shen et al., *Anal. Chem.* 2004, 76, 144). When the sample loading amount was increased to 84 pg, the number of protein and peptide identifications increased to 162±8 and 570±11, respectively (FIG. 9).

Figure 10:
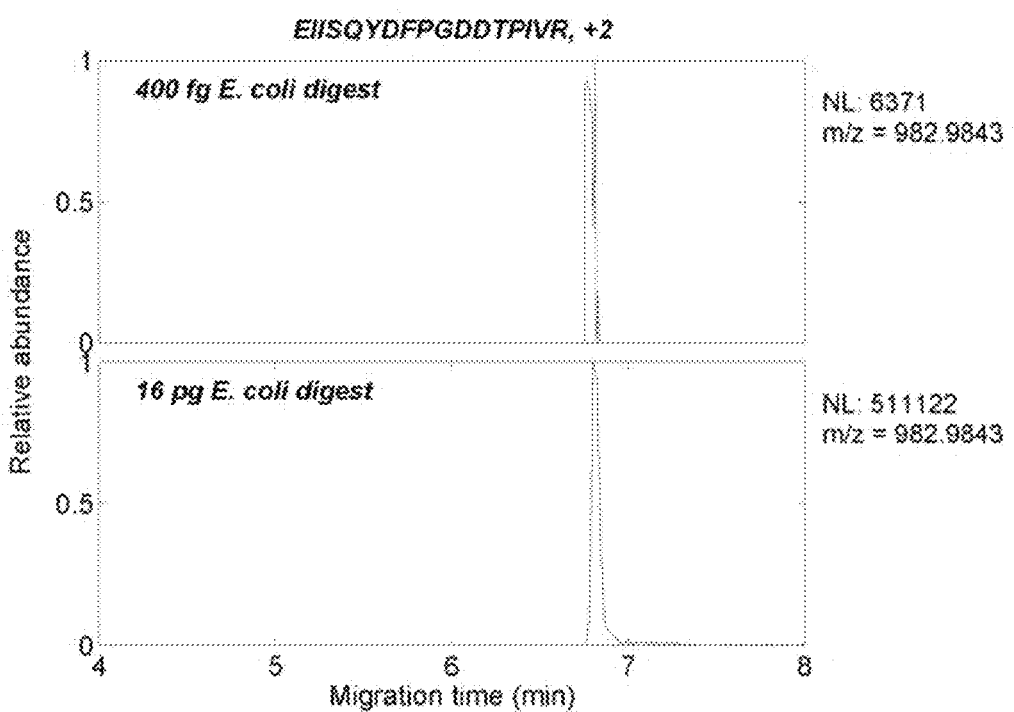
FIG. 10. Extracted ion electropherogram of an identified peptide from 400 fg (top), and the corresponding electropherogram from a 16 pg amount of E. coli digests (bottom), based on accurate mass and time tags (AMTs) method (153 additional pair of electropherograms not shown). The mass tolerance used for peak extraction was 3 ppm.

We also applied Smith's accurate mass and time tag approach using the 16 pg E. coli data as the database. Over 60 proteins and 150 peptides were identified from the 400 fg E. coli digests with mass tolerance as 3 ppm, migration time tolerance as 0.3 min (without alignment), and at least two detected isotopic peaks for each peptide (FIG. 9). A representative extracted ion electropherograms is shown in FIG. 10. This result is a 20-times improvement in the number of protein identifications in the state of art for AMTs based sub-picogram proteome analysis.

Figure 11A:
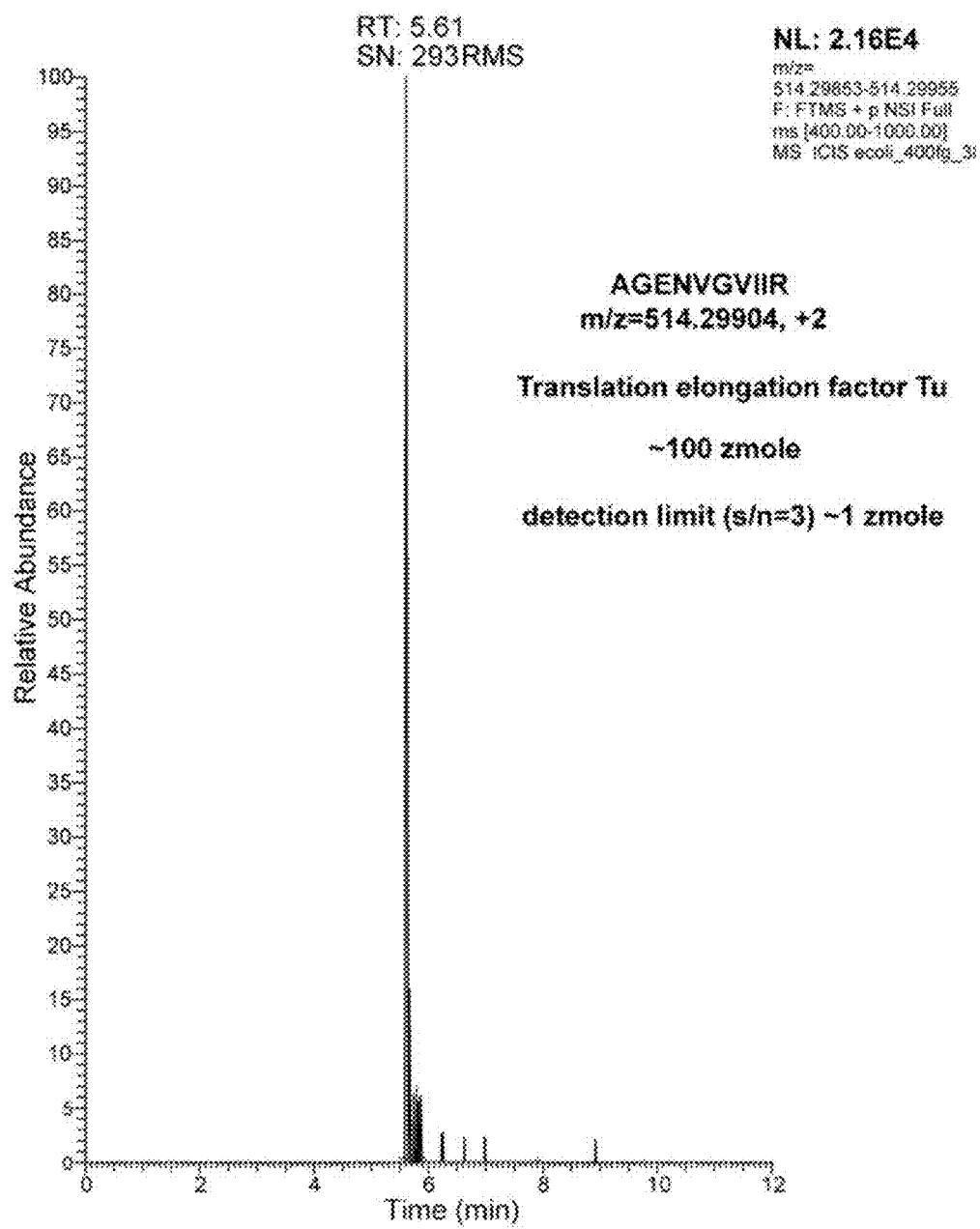
FIGS. 11A-C. The extracted ion electropherograms of three elongation factor Tu peptides (FIGS. 11A, 11B, and 11C) identified with MS/MS from 400 fg amounts of E. coli digests for calculation of peptide detection limits.
Figure 11B:
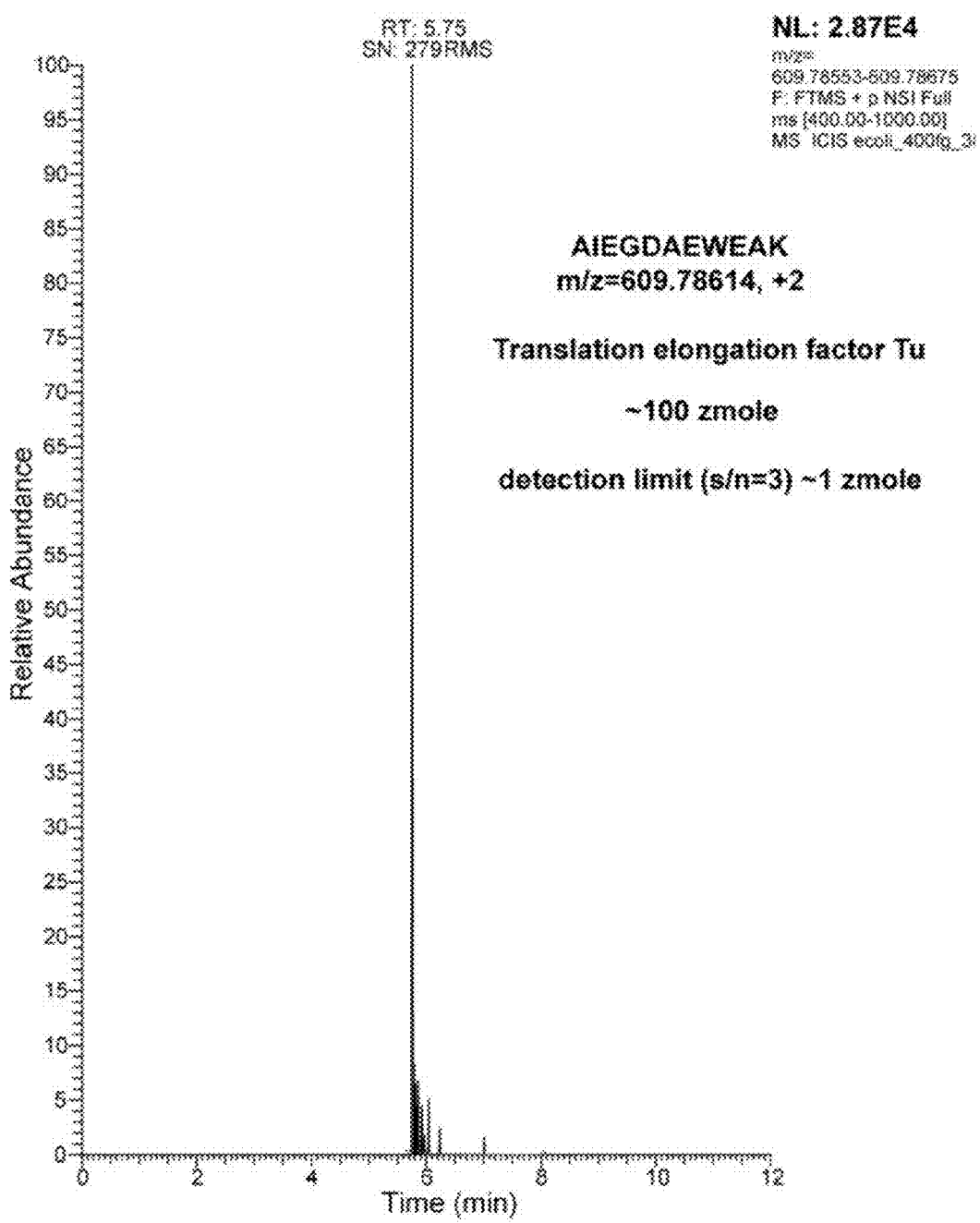
Figure 11C:
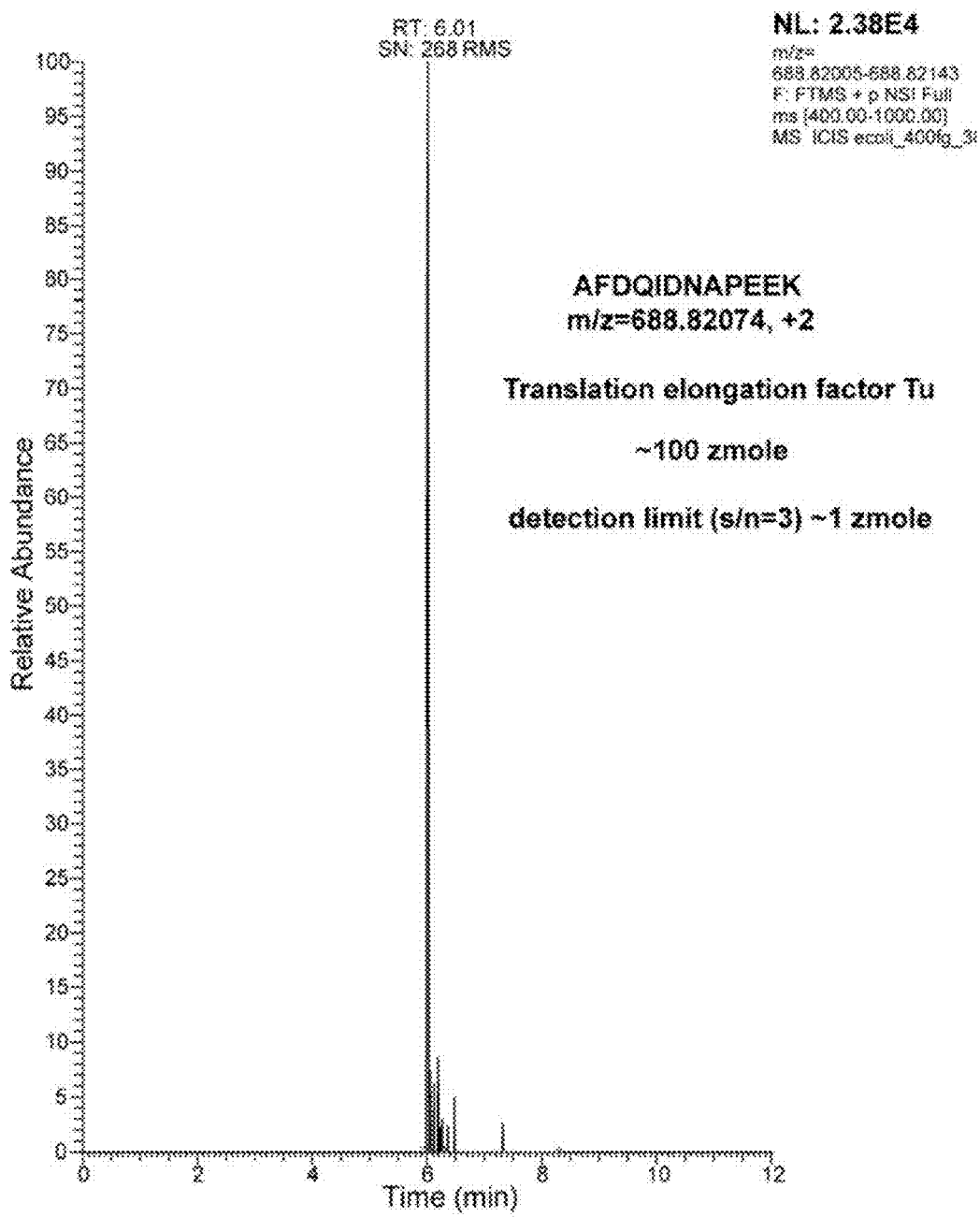

We finally estimated the peptide detection limit from the 400 fg E. coli data. We manually extracted electropherograms for three peptides from elongation factor Tu, which were identified based on MS/MS spectra with mass tolerance of 1 ppm. The signal-to-noise ratios were obtained with Xcalibur software (Thermo Fisher Scientific), using the noise region from 0.3 min to 2.3 min after the peak (FIG. 11). Based on the amount of elongation factor Tu present in the sample (4 fg) and its molecular weight (~43 kDa), ~100 zmole of these peptides were taken for analysis. These peptides generated signal-to-noise ratios (S/N) of 270~290; the mass detection limit (S/N=3) is ~1 zmole (~600 molecules), which is a one order of magnitude improvement in the state of art for MS based peptide detection.

Explanations for the high sensitivity obtained from the CZE-MS system include the following. First, the peptides only take about 0.2 s or less to migrate from the capillary end to the spray emitter end (approximately calculated based on our work), which dramatically reduces the sample diffusion in the spray emitter and generates a higher peptide signal, resulting in better peptide detection limits. Second, the electroosmotic flow rate in the separation capillary and in the spray emitter is approximately the same due to similar buffer and applied voltage (~300 V/cm), and the total flow rate for spray is around 20 nL/min, which generates high ionization efficiency, resulting in high sensitivity. Third, we employ quite narrow inner diameter capillaries, which reduces sample flow rate and generates very efficient separations.

We also note that the number of protein identifications obtained in this work is ~200 proteins due to the relatively short peptide separation window, limiting the number of acquired tandem spectra, which limits the detection of relatively low abundance proteins in biological samples. Ways to improve the protein identifications based on the CZE-MS system are to perform online/offline peptide pre-fractionation before the CZE-MS analysis, to use a longer separation capillary to slow the separation, or to employ coated capillaries to reduce electro-osmosis and increase the separation window.

In summary, this example describes an ultrasensitive and high throughput CZE-ESI-MS/MS system for femtogram proteomics analysis. The results obtained using the system are a one- to two-orders of magnitude improvement in the amount of material required for protein identification by tandem mass spectrometry, in the number of proteins identified by accurate mass and time tags from sub-picogram amounts of a complex protein digest, in peptide mass detection limit, and in analysis time. The system can be used for single cell analysis. To date, the highest sensitivity tools available for single cell protein analysis have employed laser-induced fluorescence detection. While sensitive, fluorescence inherently generates a low-information content signal that provides only rudimentary information on protein identity. The development of CZE-mass spectrometry systems with 1-zmol detection limits opens the door to single-cell protein analysis with confident identification of relatively high abundance proteins.

Materials. Bovine pancreas TPCK-treated trypsin, urea, ammonium bicarbonate ($NH_4HCO_3$), dithiothreitol (DTT), and iodoacetamide (IAA) were purchased from Sigma-Aldrich (St. Louis, Mo.). Acetonitrile (ACN), formic acid (FA), and hydrofluoric acid (HF) were purchased from Fisher Scientific (Pittsburgh, USA). Methanol and water were purchased from Honeywell Burdick & Jackson (Wicklow, Ireland). Fused silica capillary (10 μm i.d./150 μm o.d.) was purchased from Polymicro Technologies (Phoenix, USA). Complete, mini protease inhibitor cocktail (provided in EASYpacks) was purchased from Roche (Indianapolis, USA). Equipment such as a PEEK cross, nuts, ferrules, sleeves and PHFA tubing can be purchased from suppliers such as Idex Health and Science (Oak Harbor, Wash., USA).

Preparation of the *E. coli* Sample. *E. coli* (Dh5-Alpha) was cultured with the protocol described by Faserl et al. (*Anal. Chem.* 2011, 83, 7297). After culture, the *E. coli* pellets were first washed with PBS (three times). Then, the pellets were suspended in 8 M urea and 100 mM Tris-HCl (pH 8.0) buffer containing protease inhibitor and sonicated for 15 minutes on ice for cell lysis. The lysate was centrifuged at 18,000 g for 15 minutes, followed by protein concentration measurement with the BCA method (Cohen et al., *Annu. Rev. Anal. Chem.* 2008, 1, 165). An aliquot of protein (900 μg) was precipitated by cold acetone overnight at −20° C. After centrifugation, the protein pellet was washed again with cold acetone to remove contaminants. After incubation at room temperature (~22° C.) for several minutes to dry, proteins were dissolved in 300 μL of 8 M urea in 100 mM $NH_4HCO_3$ (pH 8.5), followed by protein denaturation at 37° C. for 60 minutes, reduction with DTT (8 mM) at 60° C. for 1 hour, and alkylation with IAA (20 mM) at room temperature for 30 minutes in the dark.

Then, 1.2 mL of 100 mM NH4HCO3 (pH 8.5) was added to dilute the urea concentration to less than 2 M. Finally, an aliquot of 60 μL treated protein solution (36 μg) was digested overnight at 37° C. with trypsin at a trypsin/protein ratio of 1/30 (w/w). The digests were acidified with formic acid (FA) (0.5% final concentration) to terminate the reaction. The tryptic digests were desalted with a ZipTipC18 (Millipore, Bedford, USA), followed by lyophilization with a vacuum concentrator (Thermo Fisher Scientific, Marietta, USA). The dried protein digests were dissolved in 0.05% (v/v) FA aqueous buffer containing 20% (v/v) ACN, resulting in solutions of 0.1 mg/mL and 0.01 mg/mL concentration, which were then used for analysis.

Preparation of the Separation Capillary. A gentle flame was used to remove a 1 cm length of the polyamide coating about 3-4 cm from one end of a fused silica capillary (10 μm i.d./150 μm o.d., ~50 cm length). A reaction chamber was prepared by drilling a small hole at the bottom of a 200 μL Eppendorf tube with a drill bit that is slightly larger than the capillary outer diameter. The capillary was threaded through the hole so that the flamed portion of the capillary was held within the Eppendorf tube.

Finally, ~150 μL of hydrofluoric acid (HF, ~50% w/w) was added to the Eppendorf tube, and incubated at room temperature in the hood for ~20 minutes. After etching, the outer diameter of the etched region was about 60 μm, while the inner diameter of the capillary was unchanged because it did not come in contact with the HF. The exterior of the capillary was washed with deionized water to remove the residual HF and then the capillary was cut to ~40 cm length with a ~5 mm etched region at the distal end. Caution and appropriate safety procedures should be used while handling HF solutions. The etched capillary was successively flushed with sodium hydroxide (1 M), deionized water, hydrochloric acid (1 M), deionized water, and 0.5% (v/v) FA.

CZE-ESI-MS/MS Analysis. The capillary electrophoresis system was assembled from components reported previously (see Moini, *Anal. Chem.* 2007, 79, 4241; Li et al., *Anal. Chem.* 84, 1617-1622 (2012); Sun et al., *Anal. Chem.* 85, 4187-4194 (2013)). See also FIG. 3A. Two Spellman CZE 1000R high-voltage power supplies provided high voltage for the separation and electrospray. Voltage programming was controlled by LabView software.

The total length of separation capillary was 40 cm (for 400 fg, 4 pg, and 16 pg amounts of *E. coli* digests) or 32 cm (for 28 pg and 84 pg amounts of *E. coli* digests). The separation buffer was 0.5% (v/v) FA in deionized water, and the sheath liquid was 0.1% (v/v) FA containing 10% (v/v)

methanol. The sample was dissolved in an aqueous buffer containing 0.05% (v/v) FA and 20% (v/v) acetonitrile. The sample was injected into the separation capillary by air pressure (10-20 psi and 1-9 s), and the sample injection volume was calculated based on Poiseuille's law.

An electrokinetically pumped sheath flow interface was used to couple the capillary to the mass spectrometer. The electrospray emitter was drawn from a borosilicate glass capillary (1.0 mm o.d., 0.75 mm i.d., and 10 cm length) pulled with a Sutter instrument P-1000 flaming/brown micropipette puller. The emitter tip was ~8 μm in outer diameter and 6 μm inner diameter with a 3 mm taper. The etched end of the separation capillary was threaded through a PEEK coned port cross (Upchurch, Oak Harbor USA) into the spray emitter. The distance between the capillary tip and the emitter end was about 200 μm (see FIG. 3B and C). Sheath liquid was introduced into the electrospray tip by HPFA tubing connected to the cross. The fourth port of the cross was connected to a syringe and used to flush the emitter at the start of an experiment.

The spray voltage (HVII, FIG. 3A) was 1.2 kV in each experiments. High voltage I (HVI, FIG. 3A) was 11.2 kV for 32 cm capillary (and 13.2 kV for 40 cm capillary) to produce an electric field of ~300 V/cm across the separation capillary. An electric potential of 16.2 kV was also applied as HVI for 28 pg amounts of $E.\ coli$ digests analysis while optimizing the separation conditions.

To obtain different sample loading amounts, 0.01 mg/mL $E.\ coli$ digests in 0.05% (v/v) FA aqueous buffer containing 20% (v/v) ACN were used as the sample for 400 fg experiments, and 0.1 mg/mL $E.\ coli$ digests were used as the sample for 4- and 84-pg experiments. Each sample was analyzed in duplicate or triplicate.

A Q-Exactive mass spectrometer (Thermo Fisher Scientific) was used in experiments in data dependent acquisition mode. Full MS scans were acquired in the Orbitrap mass analyzer over m/z 380-1,800 (for 28 and 84 pg $E.\ coli$ samples) and m/z 400-1,000 (for 400 fg, 4 pg, and 16 pg of $E.\ coli$ samples) with resolution 70,000 (at m/z 200). The target values and maximum injection time were 1.00E+06 and 250 ms (for 16, 28, and 84 pg of $E.\ coli$ samples); 3.00E+06 and 500 ms (for 400 fg and 4 pg $E.\ coli$ samples).

For 400 fg of $E.\ coli$ digests analysis, two most intense peaks (Top 2 method) with charge state as 2 or 3 and intensity higher than 2.00E+03 were sequentially isolated in the quadrupole with isolation window as 2 m/z and fragmented in the higher energy collisional dissociation collision cell with normalized collision energy of 28%, and tandem mass spectra were acquired in the Orbitrap mass analyzer with resolution 35,000 (m/z 200), target value 1.00E+06, and maximum injection time 500 ms.

For 4 pg of $E.\ coli$ digests analysis, the Top 4 method was applied, and maximum injection time for tandem spectra as 250 ms. For 16 pg of $E.\ coli$ digests analysis, the Top 6 method was used. The maximum injection time for tandem spectra was 120 ms, intensity threshold was 4.00E+03, and charge exclusion was 1 and 5 and higher. For 28 and 84 pg of $E.\ coli$ digests analysis, the Top 6 method was used. The maximum injection time for tandem spectra was 120 ms, intensity threshold was 8.00E+03, and charge exclusion was 1 and 7 and higher. For each experiment, dynamic exclusion was 6.0 s, microscans was 1, peptide match was on, and exclude isotopes was on.

Data Analysis. Raw MS files were analyzed by MaxQuant software version 1.3.0.5. MS/MS spectra were searched by the Andromeda search engine (Cox et al., *J. Proteome Res.* 10, 1794) against the NCBI-$E.\ coli$ (DH1) database containing forward and reverse sequences (8,320 entries including forward and reverse sequences). The database also included common contaminants. MaxQuant analysis included an initial search with a precursor mass tolerance of 10 ppm, main search precursor mass tolerance of 5 ppm, and fragment mass tolerance of 20 ppm. The search included the enzyme as trypsin, variable modifications of methionine oxidation, N-terminal acetylation and deamidation (NQ), and fixed modification of carbamidomethyl cysteine. Minimum peptide length was set to seven amino acids and the maximum number of missed cleavages was set to two. The false discovery rate was set to 0.01 for both peptide and protein identifications. The proteins identified by the same sets of peptides were reported as one protein group. The protein and peptide tables were filtered to remove the identifications from the reverse database and common contaminants.

Example 2.

CZE-ESI-MS/MS for Quantitative Parallel Reaction Monitoring

This example describes the use of capillary zone electrophoresis-electrospray ionization-tandem mass spectrometry (CZE-ESI-MS/MS) for the quantitative parallel reaction monitoring of peptide abundance and single-shot proteomic analysis of a human cell line.

We coupled capillary zone electrophoresis (CZE) with an ultrasensitive electrokinetically pumped nanospray ionization source for tandem mass spectrometry (MS/MS) analysis of complex proteomes. We first used the system for the parallel reaction monitoring (PRM) analysis of angiotensin II spiked in 0.45 mg/mL of bovine serum albumin (BSA) digest. A calibration curve was generated between the loading amount of angiotensin II and intensity of angiotensin II fragment ions. CZE-PRM generated a linear calibration curve across over 4.5 orders of magnitude dynamic range corresponding to angiotensin II loading amount from 2 amole to 150 fmole. The relative standard deviations (RSDs) of migration time were <4% and the RSDs of fragment ion intensity were ~20% or less except 150 fmole angiotensin II loading amount data (~36% RSD).

We further applied the system for the first bottom up proteomic analysis of a human cell line using CZE-MS/MS. We generated 283 protein identifications from a 1 hour long, single-shot CZE MS/MS analysis of the MCF7 breast cancer cell line digest, corresponding to an approximately 80 ng loading amount. The MCF7 digest was fractionated using a C18 solid phase extraction column. Single-shot analysis of a single fraction resulted in 468 protein identifications, which is by far the largest number of protein identifications reported for a mammalian proteomic sample using CZE.

Capillary electrophoresis (CE)-electrospray ionization (ESI)-mass spectrometry (MS) has been used to characterize a wide range of analytes, including intact proteins, peptides, and metabolites. One useful CE-nanospray interface is a sheath-flow interface we developed that employs a glass emitter with a ~5-μm orifice (Wojcik et al., *Rapid Commun. Mass Spectrom.* 24 (2010) 2554). Electro-osmosis at the glass surface drives the sheath fluid at very low rates. The interface has several advantages, including minimal sample dilution due to the very low sheath flow rate, elimination of mechanical pumps and nebulizing gas, use of a wide range of separation buffers, and stable operation in the nanospray regime. We have applied the electrokinetically pumped sheath flow nanospray interface CE-MS/MS system for shot-gun proteomic analysis of the secretome of *Mycobac-* terium marinum (Li et al., *Anal. Chem.* 84 (2012) 1617), a fraction of yeast lysate (Wojcik et al., *Talanta* 88 (2012) 324), the *E. coli* proteome (Zhu et al., *Anal. Chim. Acta.* 810 (2014) 94), picogram amounts of RAW 264.7 cell lysate (Sun et al., *Analyst* 138 (2013) 3181), and the PC12 cell lysate (Zhu et al., *Anal. Chem.* 85 (2013) 7221). In addition, the system was also applied for top-down intact protein characterization (Sun et al., *Anal. Chem.* 85 (2013) 5989), quantitative multiple reaction monitoring (MRM) of peptide abundance (Li et al., *Anal. Chem.* 84 (2012) 6116), and phosphopeptides characterization (Mou et al., *Anal. Chem.* 85 (2013) 10692).

In Example 1 above, we described a simple modification to our interface that results in ultrasensitive performance. We etched a few millimeters of the outside of the separation capillary tip with hydrofluoric acid to reduce its outer diameter from ~150 µm to ~60 µm. This step allows the capillary tip to be placed within 200 µm of the emitter orifice, which results in a significant improvement in the system's sensitivity (Sun et al., *Angew. Chem. Int. Ed. Engl.* 52 (2013) 13661). By employing a 10 µm i.d. separation capillary, a Q-Exactive mass spectrometer, and the improved CE-MS interface, we obtained 1 zmole (1 zmol=$10^{-21}$ mol=~600 molecule) peptide detection limit (S/N=3). Over 100 proteins were identified based on tandem mass spectra from 16 pg of *E. coli* digest and 154 peptides from 60 proteins were identified from 400 fg sample loading.

Our group used the electrokinetically pumped sheath flow interface for the capillary zone electrophoresis analysis of the secretome of *M. marinum* in 2012; 140 protein groups were identified (Li et al., *Anal. Chem.* 84 (2012) 1617). We improved the peptide separation by using linear polyacrylamide coated capillary and stacking injection. Approximately 300 protein groups were identified from 100 ng of *E. coli* digests by single shot analysis in less than 1 h (Zhu et al., *Anal. Chem.* 85 (2013) 2569). The number of protein IDs was increased to 871 by analyzing seven *E. coli* digest fractions from offline C18-SPE fractionation (Yan et al., *Proteomics* 13 (2013) 2546).

We also employed a capillary isoelectric focusing MS/MS system with the electrokinetically pumped sheath flow interface for eight-plex iTRAQ based quantitative proteomic analysis of differentiating PC12 cells; 835 protein groups were identified (Zhu et al., *Anal. Chem.* 85 (2013) 7221). To our knowledge, there are no publications employing CZE-MS/MS for analysis of a human cell line.

For target proteomics research, multiple/selected reaction monitoring (MRM/SRM) is typically employed with triple-quadrupole (QqQ) mass spectrometer. Briefly, the parent ion of a targeted peptide is isolated in the first quadrupole (Q1) and then fragmented in the second quadrupole (Q2). One or several fragment ions from the targeted peptide are further isolated by the third quadrupole (Q3) for detection. Recently, a new target proteomics technique was introduced, named parallel reaction monitoring (PRM), which was performed with a bench-top quadrupole-Orbitrap mass spectrometer (Peterson et al., *Mol. Cell. Proteomics* 11 (2012) 1475). For PRM, a target peptide is selected in the quadrupole and then fragmented in the collisional cell. The resulting fragment ions are analyzed in the Orbitrap to generate one full, high-resolution MS/MS spectrum. Because m/z ratios of fragment ions are not required during the method development step, the process is much easier than SRM/MRM. In addition, PRM has much better tolerance to the background matrix than SRM/MRM due to the high resolution of the Orbitrap analyzer.

In this example, we describe the first example of CZE-PRM. We employ our improved electrokinetically pumped sheath flow nanospray interface described above in Example 1 for peptide analysis. A standard peptide, angiotensin II, was spiked in a 0.45 mg/mL bovine serum albumin digest to evaluate the CZE-PRM system performance. We observed over four and a half orders of magnitude linear dynamic range for angiotensin II corresponding to loading amounts from 2 to 150,000 amole. We also presented the first example of CZE-MS/MS for bottom-up analysis of a human cell line. Nearly 300 proteins were identified from MCF7 whole cell lysate digest in a 1-hour single-shot CZE-MS/MS analysis with ~80 ng loading amount.

Experimental

1. Materials and Reagents. Bovine pancreas TPCK-treated trypsin, bovine serum albumin (BSA), urea, ammonium bicarbonate ($NH_4HCO_3$), dithiothreitol (DTT), iodoacetamide (IAA), and angiotensin II (human, Asp-Arg-Val-Tyr-Ile-His-Pro-Phe) were purchased from Sigma-Aldrich (St. Louis, Mo.). Acetonitrile (ACN), formic acid (FA), and hydrofluoric acid (HF) were purchased from Fisher Scientific (Pittsburgh, Pa.). Methanol and water were purchased from Honeywell Burdick & Jackson (Wicklow, Ireland). Fused silica capillary (10 and 20 µm i.d./150 µm o.d.) and linear polyacrylamide (LPA) coated capillary (50 µm i.d./150 µm o.d.) were purchased from Polymicro Technologies (Phoenix, Ariz.).

Eagle's minimal essential medium (EMEM), fetal bovine serum (FBS), GlutaMAX™ (100×), insulin, and Antibiotic-Antimycotic (Anti-Anti, 100×) were purchased from Life Technologies Corporation (Grand Island, N.Y.). Mammalian Cell-PE LB™ buffer for cell lysis was purchased from G-Biosciences (St. Louis, Mo.). Complete, mini protease inhibitor cocktail (provided in EASYpacks) was purchased from Roche (Indianapolis, Ind.).

2. Sample Preparation. Bovine serum albumin (BSA, 0.5 mg/mL) in 100 mM $NH_4HCO_3$ (pH 8.0) containing 8 M urea was denatured at 37° C. for 30 minutes, followed by standard reduction and alkylation with DTT and IAA. After dilution with 100 mM $NH_4HCO_3$ (pH 8.0) to reduce the urea concentration below 2 M, protein digestion was performed for 12 hours at 37° C. with trypsin at a trypsin/protein ratio of 1/30 (w/w). After acidification, the protein digest was desalted with a C18-SepPak column (Waters, Milford, Mass.), followed by lyophilization with a vacuum concentrator (Thermo Fisher Scientific, Marietta, Ohio). The dried sample was dissolved in 0.05% (v/v) FA to produce a 0.5 mg/mL solution and stored at −20° C. before use.

Angiotensin II solution was spiked into the BSA digest to generate five samples in 0.05% (v/v) FA containing 0.45 mg/mL BSA digest and different concentrations of angiotensin II (10 nM, 100 nM, 1 µM, 10 µM and 100 µM). Each sample was analyzed by CZE-PRM in triplicate.

The procedures for MCF7 cell culture, cell lysis, protein acetone precipitation, denaturation, reduction and alkylation used are described by Sun et al. (*J. Chromatogr. A.* 1337 (2014) 40). Briefly, after cell culture, MCF7 cells were lysed by sonication, followed by BCA protein concentration measurement, and acetone precipitation. Then, a 690 µg protein aliquot was dissolved in 8 M urea and 100 mM $NH_4HCO_3$ (pH ~8.0), denatured at 37° C. for 1 hour, and reduced in ~40 mM DTT at 37° C. for 1.5 hours, followed by alkylation with 100 mM IAA at room temperature for 30 minutes. After dilution with 100 mM $NH_4HCO_3$ (pH ~8.0) to reduce the urea concentration below 2 M, the proteins were digested by trypsin at a trypsin/protein ratio of 1/30 (w/w) overnight at 37° C. The protein digest was acidified with FA (1% final concentration), and desalted with C18-SepPak column (Waters, Milford, Mass.), followed by lyophilization. The peptide mixture was dissolved in 0.04% (v/v) FA containing 20% (v/v) ACN to get a 3.5 mg/mL sample, followed by CZE-ESI-MS and MS/MS analysis. Around 300 µg of digest was lyophilized again, and redissolved in 0.1% (v/v) FA. The digest was loaded onto a C18-SepPak SPE column (Waters), and eluted by 1 mL of 12% (v/v) ACN containing 0.1% (v/v) FA. The eluate was lyophilized and further dissolved in 28 µL of 0.04% (v/v) FA and 30% (v/v) ACN for CZE-ESI-MS/MS analysis.

3. CZE-ESI-MS/MS Analysis. The capillary electrophoresis system was assembled from components above in Example 1. Two Spellman CZE 1000R high-voltage power supplies provided voltages for separation and electrospray. An ultrasensitive electrokinetically pumped sheath flow interface was used to couple CZE to a Q-Exactive mass spectrometer (Thermo Fisher Scientific). The electrospray emitter was a borosilicate glass capillary (1.0 mm o.d., 0.75 mm i.d.) pulled with a Sutter instrument P-1000 flaming/brown micropipette puller, and the size of the emitter orifice was 8-10 µm. Voltage programming was controlled by LabView software.

For the CZE-PRM experiment, a 32 cm long capillary (10 and 20 µm i.d./150 µm o.d.) with etched tip (~60 µm o.d., 5 mm length) was used for the separation. The separation buffer was 0.5% (v/v) FA. The voltage at the injection end was 16.2 kV, and 1.2 kV was applied as spray voltage. For whole MCF7 cell lysate digest analysis, a 100 cm long capillary (20 µm i.d./150 µm o.d.) with ~5 mm length etched end (~60 µm o.d.) was employed, and the separation buffer was 0.5%(v/v) FA. For the MS1 only experiment, 29.2 kV was applied at the injection end; for MS/MS experiment in data dependent acquisition (DDA) mode, 21.2 kV was applied at the injection end. In both cases, 1.2 kV was applied for electrospray.

For analysis of the 12%(v/v) ACN eluate of MCF7 cell lysate digest from C18-SPE column, an LPA-coated capillary (62 cm, 50 µm i.d./150 µm o.d.) with ~5 mm long etched end (~70 µm o.d.) was used, and the separation buffer was 0.12% (v/v) FA. The voltage applied at injection end was 16.2 kV and 1.2 kV was applied as spray voltage.

For all the experiments, the sheath buffer was 10% (v/v) methanol and 0.1% (v/v) FA. The distance between the separation capillary end and spray emitter tip was around 200 µm. The sample was injected into the separation capillary by nitrogen pressure, and the injection volume was calculated based on Poiseuille's law. All the HF etching operations for separation capillaries were performed with the same protocol as described above in Example 1. The etched 10 and 20 µm i.d. separation capillary was successively flushed with sodium hydroxide (1 M), deionized water, hydrochloric acid (1 M), deionized water, and 0.5% (v/v) FA before use. The etched LPA-coated separation capillary (50 µm i.d.) was successively flushed with deionized water and 0.12% (v/v) FA before use.

For CZE-PRM experiment, the Q-Exactive was programmed in target-MS$^2$ mode with inclusion list as on. In the inclusion list, 523.7734 and +2 were set as the target m/z and charge, respectively. The normalized collisional energy (NCE) was 25%. The other parameters were as follows: resolution for MS/MS as 17,500, AGC target as 5E5, a maximum injection time as 500 ms, isolation window as 1 m/z, and microscans as 1.

For analysis of the human cell line digest, both MS1-only and regular DDA mode experiments were performed. For the MS1-only experiment, MS spectra were acquired with 380-1800 m/z range, 70,000 resolution (at m/z 200), AGC target as 1E6, maximum injection time as 250 ms, and microscans as 1. For the DDA mode experiment, a top 12 method was employed. For MS1 full scan, the parameters were the same as the MS1-only experiment. For MS/MS, twelve most intense peaks from the MS spectrum were sequentially isolated in the quadrupole (isolation window as 2.0 m/z) and further fragmented in the higher energy collisional dissociation (HCD) cell (NCE as 28%), followed by Orbitrap analysis. Resolution of 35,000 (at m/z 200), AGC target as 1E6, maximum injection time as 120 ms, and microscans as 1 were applied. The parent ions with charge states higher than +1 and intensity higher than 8.3E3 were chosen for fragmentation. Dynamic exclusion was set as 10 s for 20 µm i.d. capillary and 15 s for 50 µm i.d. capillary. Peptide match and exclude isotopes were turned on.

4. Data Analysis. For CZE-PRM experiment, the data were manually analyzed with Thermo Xcalibur software. The peaks of fragment ions from angiotensin II were manually extracted with 10 ppm mass tolerance and Gaussian smoothing (5 points) was performed on the peaks.

For human cell lysate digest data, the raw files containing tandem spectra were analyzed with Proteome Discoverer 1.3 software (Thermo Fisher Scientific). Mascot 2.2 was used for database searching against Swiss-Prot database with taxonomy as human (20,335 sequences). Trypsin was chosen as the digestion enzyme, and the maximum number of missed cleavages was set as 2. The mass tolerances for parent ions and fragment ions were set as 10 ppm and 0.05 Da, respectively. Dynamic modifications included oxidation (M), deamidation (NQ), and acetylation (K and protein N-terminus). Carbamidomethylation (C) was set as the fixed modification. Database searching against the corresponding reversed database was also performed in order to evaluate the false discovery rate (FDR) (Elias and Gygi, Nat. Methods 4 (2007) 207).

Percolator software (version 1.17) integrated in the Proteome Discoverer 1.3 was used to evaluate the database searching results. For peptide level analysis, peptide confidence value as high was used to filter the peptide identification, corresponding to peptide-level FDR less than 1%. For peptides per protein settings, the following parameters were applied, including minimal number of peptides as 1, count only rank 1 peptides, and count peptide only in top scored proteins. In addition, protein grouping was enabled.

Results and Discussion

1. CZE-PRM for Peptide Detection. For CZE-PRM experiments, the Q-Exactive was programmed in target-MS$^2$ mode. In the inclusion list, m/z 523.7734 (+2) corresponding to angiotensin II (human, Asp-Arg-Val-Tyr-Ile-His-Pro-Phe) was used. The angiotensin II standard peptide was spiked into a 0.45 mg/mL BSA digest to generate a series of samples containing 10 nM, 100 nM, 1 µM, 10 µM, and 100 µM of angiotensin II, corresponding to 15 amole to 150 fmole of angiotensin II loaded onto the separation capillary (20 µm i.d.) in the presence of a constant background of BSA digest.

Figure 12:
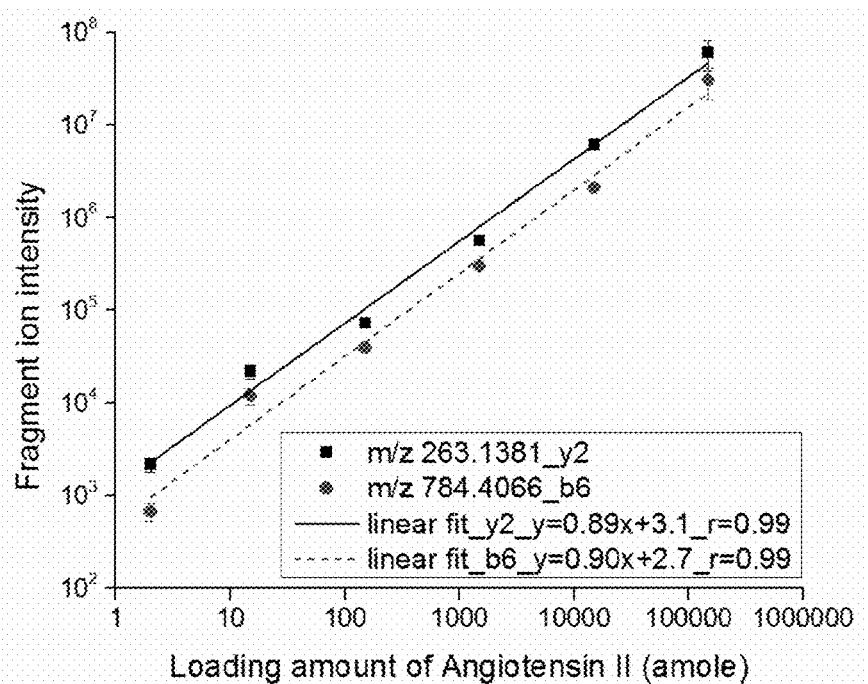
FIG. 12. Wide dynamic range calibration curve for loading amounts and fragment ions (y2$^+$ and b6$^+$) intensity of angiotensin II after CZE-PRM analysis. The lines are the results of unweighted linear fit to the log-log data.

We also employed a 10 µm i.d. separation capillary to analyze a sample made from 10 nM angiotensin II spiked in a 0.45 mg/mL BSA digest. In this experiment, about 2 amole of angiotensin II was loaded onto the capillary. After triplicate CZE-PRM analyses, the two most intense fragment ions ($b6^+$ and $y2^+$) of angiotensin II were extracted from the acquired data with 10 ppm mass tolerance to construct a calibration curve (FIG. 12). We performed an unweighted weighting linear fit to the log-log data. The fragment ion signal increased linearly with angiotensin loading amount over 4.5 orders of magnitude (log-log b6$^+$ slope=0.90, r=0.99; y2$^+$ slope=0.89, r=0.99). We note that the two fragment ions of angiotensin II co-migrate in each CZE-PRM run, which confirms the detection of the standard peptide.

Use of 2 amole of angiotensin II in the presence of the 0.45 mg/mL (~7 µM) BSA digest background generated ~2.0E+03 signal for the most abundant fragment ion (y2$^+$) of angiotensin II. This signal is ~20 times higher than that from our previous work that also injected ~2 amole of Leu-enkephalin, in the presence of 66 nM of BSA digest as background and using CZE-MRM analysis (Li et al., *Anal. Chem.* 84 (2012) 6116).

The dramatic improvement in signal amplitude is caused by several factors. First, our first-generation electrokinetically pumped sheath flow interface was employed in the earlier work, whereas the improved version of the interface (Example 1 above) was used in this work. Because the distance between separation capillary tip and spray emitter tip in the improved interface is five-times shorter than that in original version, diffusion of peptides in the spray emitter is decreased, peptide peaks are much sharper, and peptide signals are correspondingly more intense. Second, we used a separation capillary with much smaller inner diameter (10-20 µm vs. 50 µm) and separation buffer with much lower pH value (lower than 3 vs. 6-8), which reduces the flow rate in the separation capillary, generating better sensitivity. Third, online stacking was used in this work, which again sharpens peaks. The conductivity of sample matrix (0.05% (v/v) FA) is much lower than the separation buffer (0.5% FA), so that peptides are concentrated when high voltage is applied across the capillary. In addition, a much higher resolution mass analyzer (Orbitrap vs. quadrupole) was employed in this work, which generates vastly superior tolerance to the background matrix.

Figure 13:
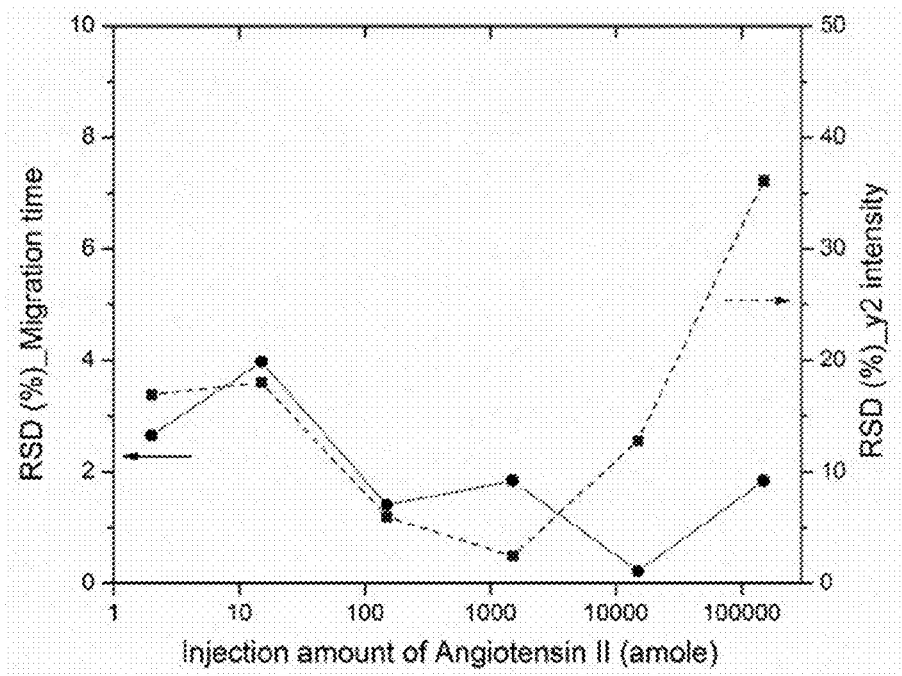
FIG. 13. Relative standard deviations (RSDs) of migration time and intensity of angiotensin II fragment ion (y2$^+$) for different loading amounts (2 amole-150 fmole) from triplicate CZE-PRM analysis.

We also evaluated the reproducibility of the CZE-PRM system in terms of migration time and intensity of angiotensin II fragment ion (y2$^+$) (FIG. 13). The relative standard deviations (RSDs) of migration time for triplicate analysis were less than 4%. The RSDs of the fragment ion intensity for triplicate analysis were ~36% for 150 fmole loading amounts, around 10% or less for 150 amole to 15 fmole loading amounts, and close to 20% for 2 and 15 amole loading amounts.

The slightly higher RSDs for the 2 and 15 amole loading amount data are likely due to two reasons. First, the intensity of co-isolated BSA peptides will be much higher than angiotensin II, leading to higher detection variation for very low loading amounts. Second, the very sharp peaks of the fragment ions (full width at half height for the peaks are ≤2 s) for the 2 and 15 amole loading amount data leads to fewer data points across the peaks than the higher loading amounts data. For the 150-fmole loading amount data, the RSD is significant higher because the CE-MS system is slightly overloaded, which produces non-Gaussian peak shapes. In addition, the RSDs data of migration time and fragment ion intensity for angiotensin II fragment ion b6$^+$ agree well with that for m y2$^+$.

2. CZE-ESI-MS and MS/MS for Human Cell Lysate Digest Analysis. Example 1 above described the use of an etched-tip electrokinetically pumped sheath flow nanospray interface based CZE-MS/MS system, which was used to analyze high-femtogram to mid-picogram amounts of E. coli cell lysate digest. That study demonstrated that the improved system was highly efficient and quantitatively reproducible for separation and detection of a prokaryote proteome digest. To date, there has been no published bottom-up analysis of a human proteome using CZE-MS/MS.

Figure 14A:
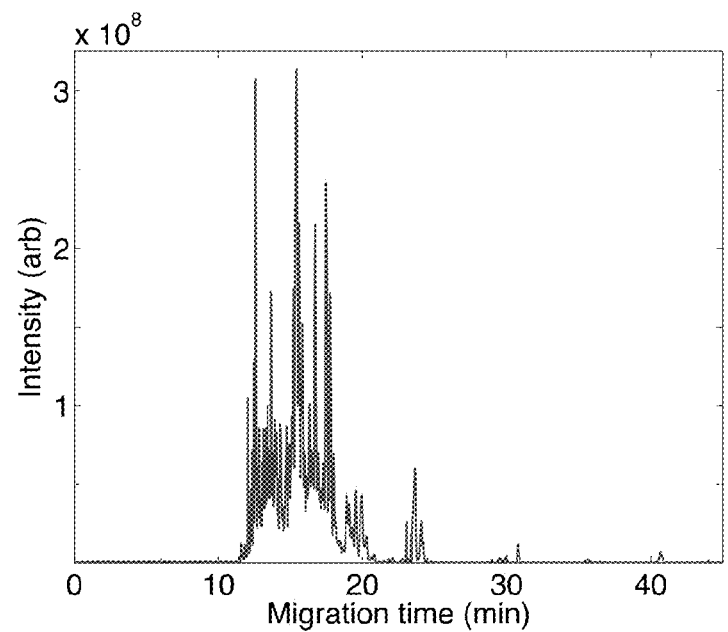
FIGS. 14A-B. Base peak electropherogram of MCF7 digest after CZE-ESI-MS analysis.
Figure 14B:
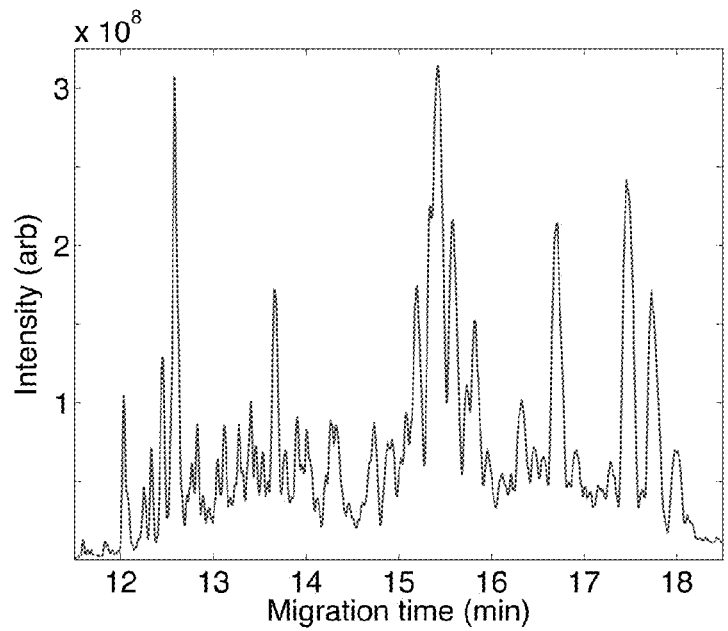

Here, we report the first application of CZE-MS/MS for the bottom-up analysis of a human proteome, the proteome of the MCF-7 human breast cancer cell line. We began by using the ultrasensitive interface for analysis of ~60 ng of a whole-cell digest (FIG. 14). The separation was driven by a 280 V/cm electric field. Peptides began to migrate from the capillary at 11 minutes, and the separation was nearly complete by 26 minutes (FIG. 14A), although a few strong peaks were observed at later times. The separation is highly efficient and peaks are very sharp (FIG. 14B).

Roughly 10-20 peaks were resolved from the base peak electropherogram across the 1-minute separation window from 13-14 minutes. We extracted one peptide (m/z 400.77161, z=+2) from the data with 2 ppm mass tolerance that generated 525,000 theoretical plates, which demonstrates the extraordinarily high separation efficient produced by this instrument.

We next applied single-shot CZE-MS/MS for bottom-up analysis of the MCF7 whole cell lysate digest. Around 80 ng of peptides was loaded onto a 100-cm long, 20 µm i.d. separation capillary. The separation was performed at 200 V/cm electric field. After database searching of the tandem spectra, 1,159 peptides and 283 proteins were confidently identified, and 176 proteins were identified based on at least two peptides. The separation was complete in roughly 40 minutes.

To test how many peptides and proteins can be identified from the MCF7 proteome with single-shot CZE-MS/MS, we simplified the MCF7 cell lysate digest by fractionating the proteome. Peptides were first trapped on a C18 SPE column and then a fraction was eluted with 12% (v/v) ACN for analysis. An LPA-coated separation capillary was used to reduce electro-osmosis, which increases the separation capacity. To increase sample injection volume, we used a 50-µm ID capillary and injected about 130 nL of sample. After database searching, the single-shot analysis identified 1,199 peptides and 468 proteins. 219 proteins were identified based on at least two peptides. The separation was complete within 60 minutes. The combined datasets contain 2,005 peptide and 537 protein IDs.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A sheath-flow interface for producing electrospray from a capillary comprising:
   (a) a silica capillary configured to contain an analyte liquid, the capillary having an injection end configured to receive the analyte liquid and an uncoated distal end configured to expel analyte effluent, wherein the outer diameter of a segment of the distal end tapers to a reduced outer diameter within the range of about 20 μm to about 200 μm;

(b) an electrospray emitter coaxially disposed surrounding at least the distal end of the capillary, the electrospray emitter having a distal end that is tapered to terminate at an opening, the opening being coaxially disposed in relation to the distal end of the capillary; and (c) a sheath liquid reservoir in liquid communication with an interior of the electrospray emitter, such that an electrically conductive sheath liquid can flow from the sheath liquid reservoir, through a connecting fixture intermediate the capillary and the electrospray emitter, across the distal end of the capillary, and through the opening at the distal end of the electrospray emitter;

wherein the sheath liquid provides electrical contact between the capillary and the electrospray emitter, the sheath-flow interface is configured to produce a nanospray generated by electrokinetic flow of the sheath liquid mixed with the analyte effluent, and the electrokinetic flow is generated by an electric potential between the electrospray emitter and a target surface disposed adjacent, but not in physical contact with, the opening of the emitter.

2. The sheath-flow interface of claim 1 wherein the distal end of the capillary is about 700 μm from the distal end of the emitter orifice to about 100 μm beyond the emitter orifice opening.

3. The sheath-flow interface of claim 2 wherein the distal end of the capillary is about 100 nm to about 250 m from the distal end of the emitter orifice.

4. The sheath-flow interface of claim 2 wherein the distal end of the capillary extends to within the termination point of the distal end of the emitter orifice to about 100 m beyond the distal end of the emitter orifice.

5. The sheath-flow interface of claim 1 wherein the outer diameter of the distal end of the capillary is about 20 μm to about 75 82 m.

6. The sheath-flow interface of claim 1 wherein the segment of the distal end that tapers to a reduced outer diameter comprises a segment length of about 0.1 mm to about 10 mm.

7. The sheath-flow interface of claim 1 wherein the distal end of the capillary is about 250 μm from the distal end of the emitter orifice to about 100 μm beyond the emitter orifice opening and wherein the sheath-flow interface can detect a plurality of peptides from a 400 femtogram sample of peptides in less than 12 minutes when configured with capillary zone electrophoresis and a tandem mass spectrometer.

8. The sheath-flow interface of claim 7 wherein the peptides comprise an *E. coli* tryptic digest.

9. The sheath-flow interface of claim 7 wherein the mass spectrometer detection limit is about 1-10 zeptomoles.

10. The sheath-flow interface of claim 7 wherein the mass spectrometer detection limit is approximately 1 zeptomole.

11. The sheath-flow interface of claim 1 wherein the distal end of the capillary is about 500 μm from the distal end of the emitter orifice to about 100 μm beyond the emitter orifice opening, the sheath-flow interface is configured for an electrokinetic flow rate of about 15 nL/min to about 200 nL/min and is configured with a capillary zone electrophoresis instrument and a mass spectrometer, wherein greater than 150 peptides can be identified by accurate mass and time tags from sub-picogram amounts of a complex protein digest in less than 12 minutes of mass spectrometer time.

12. A method to analyze a protein digest comprising configuring the sheath-flow interface of claim 1 with a capillary zone electrophoresis instrument, wherein the analyte liquid is separated within a separation capillary by capillary zone electrophoresis, and about 10 kV of potential is applied to provide an electric field of about 300 V/cm, to produce a wide analyte separation window, during which time analytes migrate from the capillary into the interface within about 60 minutes.

13. The method of claim 12 wherein an average of 250,000 theoretical plates to about 350,000 theoretical plates are obtained for peptide separations.

14. The method of claim 12 wherein the inner diameter of the separation capillary of the sheath-flow interface is about 5 μm to about 75 μm.

15. The method of claim 12 wherein the total flow rate for spray is about 20-200 nL/minute.

16. The method of claim 12 comprising configuring the sheath-flow interface of claim 1 with tandem mass spectrometry, wherein the sheath-flow interface is configured to provide the nanospray to a mass spectrometer for analysis, wherein the target surface is an input orifice of the mass spectrometer, and wherein the lower detection limit of protein samples is about 3 femtograms to about 5 femtograms.

17. The method of claim 16 wherein the mass detection limit of peptides analyzed is about 1 zeptomole.

18. The method of claim 16 wherein the signal-to-noise ratio of peptides analyzed is about 260:1 to about 300:1.

19. A method for producing a nanospray of an analyte effluent from a capillary using a sheath-flow interface according to claim 1, comprising applying a voltage to the sheath liquid reservoir sufficient to drive electroosmotic flow of the sheath liquid from the sheath liquid reservoir, through a connecting fixture intermediate the capillary and the electrospray emitter, across the distal end of the capillary, and through the opening at the distal end of the electrospray emitter, wherein the analyte effluent is separated within the capillary by capillary zone electrophoresis by applying a voltage to the injection end of the capillary.

* * * * *